US011324249B2

(12) United States Patent
Sebastian et al.

(10) Patent No.: US 11,324,249 B2
(45) Date of Patent: May 10, 2022

(54) AEROSOL DELIVERY DEVICE WITH NANOCELLULOSE SUBSTRATE

(71) Applicant: R.J. Reynolds Tobacco Company, Winston-Salem, NC (US)

(72) Inventors: Andries Don Sebastian, Winston-Salem, NC (US); John-Paul Mua, Advance, NC (US); Luis Monsalud, Kernersville, NC (US); Stephen Benson Sears, Siler City, NC (US); Jennifer Rowe, Clemmons, NC (US); Cynthia Stokes, Lexington, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 461 days.

(21) Appl. No.: 16/294,098

(22) Filed: Mar. 6, 2019

(65) Prior Publication Data

US 2020/0281249 A1 Sep. 10, 2020

(51) Int. Cl.
*A24B 15/167* (2020.01)
*A61M 11/04* (2006.01)
(Continued)

(52) U.S. Cl.
CPC ............ *A24B 15/167* (2016.11); *A24B 15/14* (2013.01); *A24B 15/165* (2013.01);
(Continued)

(58) Field of Classification Search
CPC ........... A24D 1/22; A24D 1/025; A24F 42/10; A24F 42/20
See application file for complete search history.

(56) References Cited

U.S. PATENT DOCUMENTS 4,674,519 A 6/1987 Kertitsis et al.
4,793,365 A 12/1988 Sensabaugh et al.
(Continued)

FOREIGN PATENT DOCUMENTS

CN 105167182 12/2015
CN 107212457 9/2017
(Continued)

OTHER PUBLICATIONS

Smooth and flexible filler-nanocellulose composite structure for printed electronics applications, Cellulose (2012) 19: pp. 821-829) (Year: 2012).*

(Continued)

*Primary Examiner* — Eric Yaary
*Assistant Examiner* — Jennifer A Kessie
(74) *Attorney, Agent, or Firm* — Womble Bond Dickinson (US) LLP

(57) ABSTRACT

The present disclosure provides an aerosol delivery device comprising an aerosol source member. In an example embodiment, an aerosol source member of the present disclosure may comprise a substrate portion comprising a nanocellulose material impregnated with an aerosol precursor composition, a heat source configured to heat the aerosol precursor composition from the substrate portion forming an aerosol, and an aerosol pathway extending from the substrate portion to a mouth-end of the aerosol delivery device.

24 Claims, 6 Drawing Sheets

(51) Int. Cl.
  *A24B 15/14*  (2006.01)
  *A24B 15/16*  (2020.01)
  *A24B 15/28*  (2006.01)
  *A24D 1/14*  (2006.01)

(52) U.S. Cl.
  CPC .......... *A24B 15/284* (2013.01); *A24B 15/286* (2013.01); *A24D 1/14* (2013.01); *A61M 11/042* (2014.02); *A61M 11/047* (2014.02); *A61M 2205/8206* (2013.01)

(56) References Cited

U.S. PATENT DOCUMENTS

| | | |
|---|---|---|
| 4,807,809 A | 2/1989 | Pryor et al. |
| 4,836,224 A | 6/1989 | Lawson et al. |
| 4,889,143 A | 12/1989 | Pryir et al. |
| 4,922,901 A | 5/1990 | Brooks et al. |
| 4,924,887 A | 5/1990 | Raker et al. |
| 4,924,888 A | 5/1990 | Perfetti et al. |
| 4,941,484 A | 7/1990 | Clapp et al. |
| 4,947,874 A | 8/1990 | Brooks et al. |
| 4,972,854 A | 11/1990 | Kiernan et al. |
| 4,987,906 A | 1/1991 | Young et al. |
| 5,025,814 A | 6/1991 | Raker et al. |
| 5,056,537 A | 10/1991 | Brown et al. |
| 5,060,671 A | 10/1991 | Counts et al. |
| 5,093,894 A | 3/1992 | Deevi et al. |
| 5,099,864 A | 3/1992 | Young et al. |
| 5,101,839 A | 4/1992 | Jakob et al. |
| 5,143,097 A | 9/1992 | Sohn et al. |
| 5,159,942 A | 11/1992 | Brinkley et al. |
| 5,220,930 A | 6/1993 | Gentry |
| 5,228,460 A | 7/1993 | Sprinkel, Jr. et al. |
| 5,322,075 A | 6/1994 | Deevi et al. |
| 5,322,076 A | 6/1994 | Brinkley et al. |
| 5,339,838 A | 8/1994 | Young et al. |
| 5,353,813 A | 10/1994 | Deevi et al. |
| 5,360,023 A | 11/1994 | Blakley et al. |
| 5,377,698 A | 1/1995 | Litzinger et al. |
| 5,468,936 A | 11/1995 | Deevi et al. |
| 5,498,850 A | 3/1996 | Das |
| 5,498,855 A | 3/1996 | Deevi et al. |
| 5,501,237 A | 3/1996 | Young et al. |
| 5,530,225 A | 6/1996 | Hajaligol |
| 5,551,451 A | 9/1996 | Riggs et al. |
| 5,573,692 A | 11/1996 | Das et al. |
| 5,591,368 A | 1/1997 | Fleischhauer et al. |
| 5,665,262 A | 9/1997 | Hajaligol |
| 5,697,385 A | 12/1997 | Seymour et al. |
| 6,216,707 B1 | 4/2001 | Kumar et al. |
| 6,701,936 B2 | 3/2004 | Shafer et al. |
| 7,011,096 B2 | 3/2006 | Li et al. |
| 7,017,585 B2 | 3/2006 | Li et al. |
| 7,025,066 B2 | 4/2006 | Lawson et al. |
| 7,290,549 B2 | 11/2007 | Banerjee et al. |
| 7,398,783 B2 | 7/2008 | Biggs et al. |
| 7,615,184 B2 | 11/2009 | Lobovsky |
| 7,647,932 B2 | 1/2010 | Cantrell et al. |
| 7,726,320 B2 | 6/2010 | Robinson et al. |
| 7,836,897 B2 | 11/2010 | Borschke et al. |
| 8,430,106 B2 | 4/2013 | Potter et al. |
| 8,881,737 B2 | 3/2014 | Collett et al. |
| 8,839,799 B2 | 9/2014 | Conner et al. |
| 9,215,895 B2 | 1/2015 | Bowen et al. |
| 9,078,473 B2 | 7/2015 | Worm et al. |
| 9,149,072 B2 | 10/2015 | Conner et al. |
| 9,254,002 B2 | 2/2016 | Chong et al. |
| 9,974,334 B2 | 5/2018 | Dooley et al. |
| 10,196,778 B2 | 2/2019 | Sebastian et al. |
| 2004/0255968 A1 | 12/2004 | Perfetti et al. |
| 2005/0066986 A1 | 3/2005 | Nestor et al. |
| 2007/0215167 A1 | 9/2007 | Crooks et al. |
| 2008/0236602 A1 | 10/2008 | Bereman |
| 2009/0044818 A1 | 2/2009 | Takeuchi et al. |
| 2010/0068154 A1* | 3/2010 | Sharma ............... A61M 15/025 424/40 |
| 2013/0008457 A1 | 1/2013 | Zheng et al. |
| 2013/0255702 A1 | 10/2013 | Griffith et al. |
| 2014/0096781 A1 | 4/2014 | Sears et al. |
| 2015/0020823 A1 | 1/2015 | Lipowiez et al. |
| 2015/0020830 A1 | 1/2015 | Koller et al. |
| 2015/0313283 A1 | 11/2015 | Collett et al. |
| 2016/0007652 A1* | 1/2016 | Taluskie ............... A61M 11/041 131/328 |
| 2017/0027220 A1 | 2/2017 | Sebastian et al. |
| 2017/0181474 A1* | 6/2017 | Cameron ................ A24F 40/48 |
| 2017/0291757 A1 | 10/2017 | Sebastian et al. |
| 2018/0020722 A1 | 1/2018 | Davis et al. |
| 2018/0020723 A1 | 1/2018 | Davis et al. |
| 2018/0279673 A1 | 10/2018 | Sebastian et al. |
| 2019/0082735 A1 | 3/2019 | Phillips et al. |
| 2019/0124979 A1 | 5/2019 | Sebastian et al. |
| 2019/0261685 A1 | 8/2019 | Sebastian et al. |
| 2019/0281891 A1 | 9/2019 | Hejazi et al. |
| 2020/0093182 A1 | 3/2020 | Monsalud et al. |

FOREIGN PATENT DOCUMENTS

| | | | |
|---|---|---|---|
| WO | WO 2016/067226 | 5/2016 | |
| WO | WO-2016067226 A1 * | 5/2016 | ............. A24B 15/12 |
| WO | WO 2019/073225 | 4/2019 | |
| WO | WO 2020/025723 | 2/2020 | |
| WO | WO 2020/025732 | 2/2020 | |

OTHER PUBLICATIONS

U.S. Appl. No. 15/923,735, filed Mar. 16, 2018, Hejazi et al.
Bombick et al., Fund. Appl. Toxicol., 39, p. 11-17 (1997).
*Chemical and Biological Studies on New Cigarette Prototypes that Heat Instead of Burn Tobacco*, R. J. Reynolds Tobacco Company Monograph (1988).
Chengyu et al., From Hydrophilicity to Hydrophobicity: A Critical Review—Part II: Hydrophobic Conversion, The Society of Wood Science and Technology, Wood and Fiber Science, V. 43(1), pp. 41-56, Jan. 2011.
Dufresne, "Nanocellulose: a new ageless bio nanomaterial," Materials Today, 2013, vol. 16(6), pp. 220-227.
Forsstrom, VTT Technical Research Centre of Finland, From Nanocellulose Science towards Applications, 2012 TAPPI International Conference on Nanotechnology for Renewable Materials, Jun. 5-7, 2012; Montteal, Quebec, Canada.
Garcia et al., "Industrial and crop wastes: A new source for nanocellulose biorefinery," Industrial Crops and Products, Elsevier, NI, vol. 93, Jun. 21, 2016, pp. 26-38.
Henriksson et al., "Cellulose Nanopaper Structures ofHigh Toughness," Biomacromolecules 2008, vol. 9, pp. 1579-1585.
Lavoine et al, "Microfibrillated cellulose—its barrier properties and applications in cellulosic materials: a review," J. Carbohydr. Polym. 2012, 90, pp. 735-764.
Leung, Alfred C. W., et al., Characteristics and Properties of Carboxylated Cellulose Nanocrystals Prepared from a Novel One-Step Procedure, Wiley-VCH Verlag GmbH & Co. KGaA, Weinheim, Small 2011, 7, No. 3, 302-305; Dec. 22, 2010.
Missoum et al., "Nanofibrillated Cellulose Surface Modifications: A Review," Materials, 2013, vol. 6, pp. 1745-1766.
Osterberg et al., "A Fast Method to Produce Strong NFC Films as a Platform for Barrier and Functional Materials," ACS Appl. Mater. Interfaces 2013, vol. 5, pp. 4640-4647.
Paakko et al., "Enzymatic Hydrolysis Combined with Mechanical Shearing and High-Pressure Homogenization for Nanoscale Cellulose Fibrils and Strong Gels," Biomacromolecules, American Chemical Society, US, vol. 8, Jan. 1, 2007, pp. 1934-1941.
Peng et al., "Chemistry and Applications of nanocrystalline cellulose and its derivatives: A nanotechnology perspective," Canadian Journal of Chemical Engineering, 2011, vol. 9999, pp. 1-16.
Qing et al., "A comparative study of cellulose nanofibrils disintegrated via multiple processing approaches," Carbohydrate Polymers, Applied Science Publishers, Ltd. Barking, GB, vol. 97, No. 1, May 4, 2013, pp. 226-234.

(56) References Cited

OTHER PUBLICATIONS

Torvinen et al., Smooth and flexible filler—nanocellulose composite structure for printed electronics applications. Cellulose, 2012, pp. 821-829.
Tuzzin et al., "Nanofibrillated cellulose from tobacco industry wastes," Carbohydrate Polymers, Applied Science Publishers, Ltd. Barking, GB, vol. 148, Apr. 12, 2016, pp. 69-77.
Vartiainen et al., "Hydrophobization of cellophane and cellulose nanofibrils films by supercritical state carbon dioxide impregnation with walnut oil," Biorefinery, vol. 31, No. 4, (2016).
Zhang, Yi-Heng Percival et al., "Toward and Aggregated Understanding of Enzymatic Hydrolysis of Cellulose: Noncomplexed Cellulase Systems," Wiley Interscience, *Biotechnology and Bioengineering*, vol. 88, No. 7, Dec. 30, 2004, pp. 797-824.

\* cited by examiner

US 11,324,249 B2

AEROSOL DELIVERY DEVICE WITH NANOCELLULOSE SUBSTRATE

BACKGROUND

Field of the Disclosure

The present disclosure relates to aerosol delivery devices and uses thereof for yielding aerosol precursor compositions in inhalable form. More particularly, the present disclosure relates to aerosol source members containing substrate materials for aerosol delivery devices and systems, such as smoking articles, that utilize electrically-generated heat or combustible ignition sources to heat aerosol precursor compositions, preferably without significant combustion, in order to provide an inhalable substance in the form of an aerosol for human consumption.

Description of Related Art

Many smoking articles have been proposed through the years as improvements upon, or alternatives to, smoking products based upon combusting tobacco for use. Some example alternatives have included devices wherein a solid or liquid fuel is combusted to transfer heat to tobacco or wherein a chemical reaction is used to provide such heat source. Additional example alternatives use electrical energy to heat tobacco and/or other aerosol generating substrate materials, such as described in U.S. Pat. No. 9,078,473 to Worm et al., which is incorporated herein by reference in its entirety.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference in their entireties.

Articles that produce the taste and sensation of smoking by electrically heating tobacco, tobacco-derived materials, or other plant derived materials have suffered from inconsistent performance characteristics. For example, some articles have suffered from inconsistent release of flavors or other inhalable materials and inadequate loading of aerosol precursor compositions on substrates. Accordingly, it can be desirable to provide a smoking article that can provide the sensations of cigarette, cigar, or pipe smoking, that does so without combusting the substrate material and that does so with advantageous performance characteristics.

BRIEF SUMMARY

The present disclosure relates to a nanocellulose substrate for aerosol delivery devices configured to produce aerosol and which aerosol delivery devices, in some embodiments, may be referred to as smoking articles. In one aspect, an aerosol delivery device is provided that comprises an aerosol source member. The device further includes a substrate portion comprising a nanocellulose material impregnated with an aerosol precursor composition, a heat source configured to heat the aerosol precursor composition from the substrate portion forming an aerosol, and an aerosol pathway extending from the substrate portion to a mouth-end of the aerosol delivery device.

In some embodiments, the heat source may comprise either an electrically-powered heating element or a combustible ignition source. In certain embodiments, the heat source may be a combustible ignition source comprising a carbon-based material. In certain other embodiments, the heat source may be an electrically-powered heating element comprising a power source electronically connected to a heating element. Further, the heat source may comprise a controller configured to control the power transmitted by the power source to the heating element. In certain embodiments, the heat source comprises a conductive ink printed on a surface of the substrate portion.

In certain embodiments, the nanocellulose referred to may contain at least one average particle size dimension in the range of about 1 nm to about 100 nm. In certain embodiments, the nanocellulose material may comprise cellulose microfibrils (CMFs), cellulose nanofibrils (CNFs), cellulose nanocrystals (CNCs), or combinations thereof. Additionally, the nanocellulose material may comprise a tobacco-derived nanocellulose.

In some embodiments, the nanocellulose material is impregnated with an aerosol precursor composition in a loading of least about 20%, at least about 25%, at least about 30% by weight, at least about 35% by weight, at least about 40% by weight, at least about 45% by weight, or at least about 50% by weight, based on a total weight of the impregnated material. In some aspects, the aerosol precursor composition may comprise glycerin, propylene glycol, menthol, other aerosol precursors (e.g., other polyols), or combinations thereof. In some embodiments, the nanocellulose material may be inherently hydrophobic as a result of the manufacturing process used for making the nanocellulose material. In certain other embodiments, at least a portion of the nanocellulose material is treated prior to being impregnated with the aerosol precursor composition to increase hydrophobicity. Advantageously, such treatment allows the nanocellulose material to be loaded with hydrophobic aerosol precursor components such as those selected from the group consisting of esters, terpenes (including cyclic terpenes), aromatics, and lactones. In certain embodiments, the nanocellulose material may be loaded with one or more of methyl butyrate, ethyl butyrate, isoamyl acetate, pentyl pentanoate, citral, nerol, limonene, citronella, menthol, carvone, eugenol, anisol, benzaldehyde, massoia lactone, sotolon, jasmine lactone, gamma-decalactone, geraniol, and delta-decalactone.

In certain embodiments, the substrate portion is in a particulate or shredded form, in the form of a sheet, or in the form of a film. In some embodiments, substrate portions in the form of a sheet or a film may be formed without a polymeric binder, such as embodiments that are substantially free of polymeric binder. In various other embodiments, substrate portions may be in the form of a reconstituted tobacco or botanical sheet or film formed with a polymeric binder. In some embodiments, substrate portions may be in the form of a nanocellulose sheet formed with a polymeric binder that does not comprise tobacco or botanicals, such as embodiments that are substantially free of tobacco or non-tobacco botanicals. In certain embodiments, the substrate portion may further comprise one or more of a burn retardant material and a flavorant. In some embodiments, the substrate portion may be formed in a substantially cylindrical shape. In various embodiments, the substrate portion may comprise a series of overlapping layers of a composite substrate sheet, wherein the composite substrate sheet includes a nanocellulose film or layer.

In some embodiments, the substrate portion may not comprise tobacco or nicotine, such as embodiments that are substantially free of tobacco or nicotine. In some embodiments, the substrate portion may further comprise one or more of a non-tobacco-derived nicotine and a flavorant. In certain embodiments, the substrate portion may further comprise one or more pharmaceutical agents. In some embodiments, the substrate portion may further comprise one or more non-tobacco botanicals.

These and other features, aspects, and advantages of the disclosure will be apparent from a reading of the following detailed description together with the accompanying drawings, which are briefly described below.

BRIEF DESCRIPTION OF THE FIGURES

Figure 1:
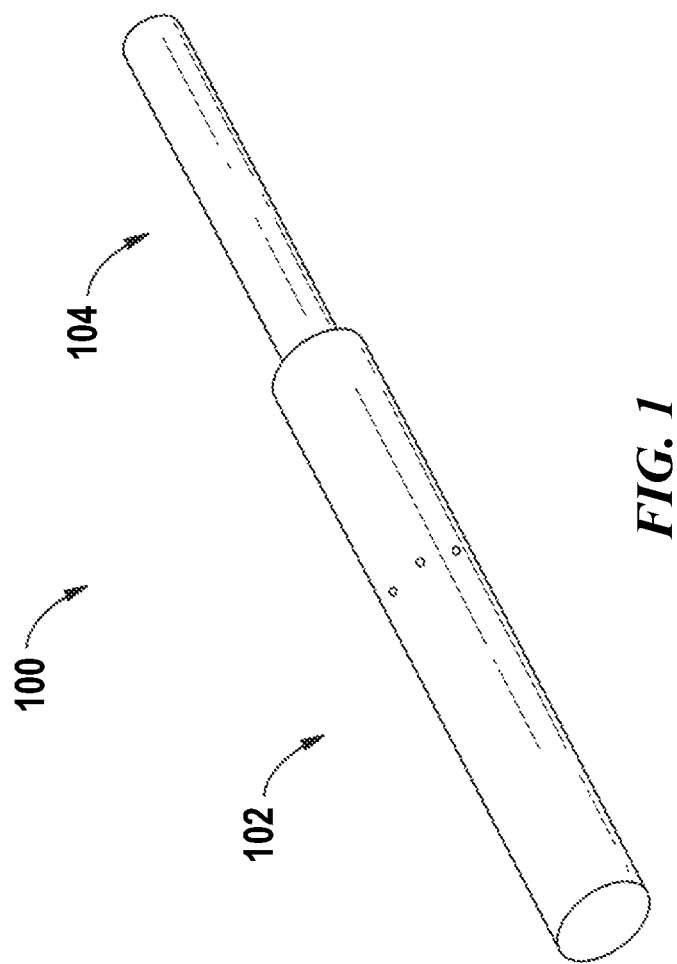
Figure 2:
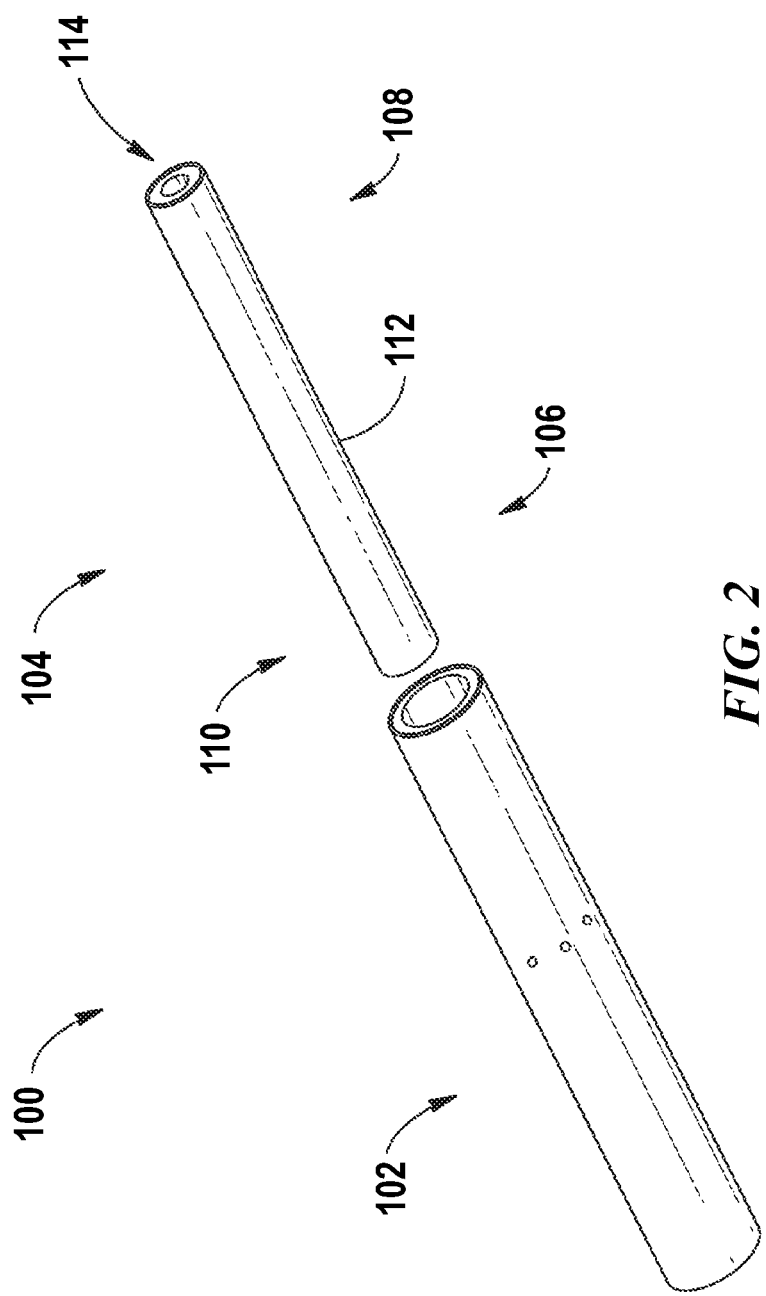
Figure 3:
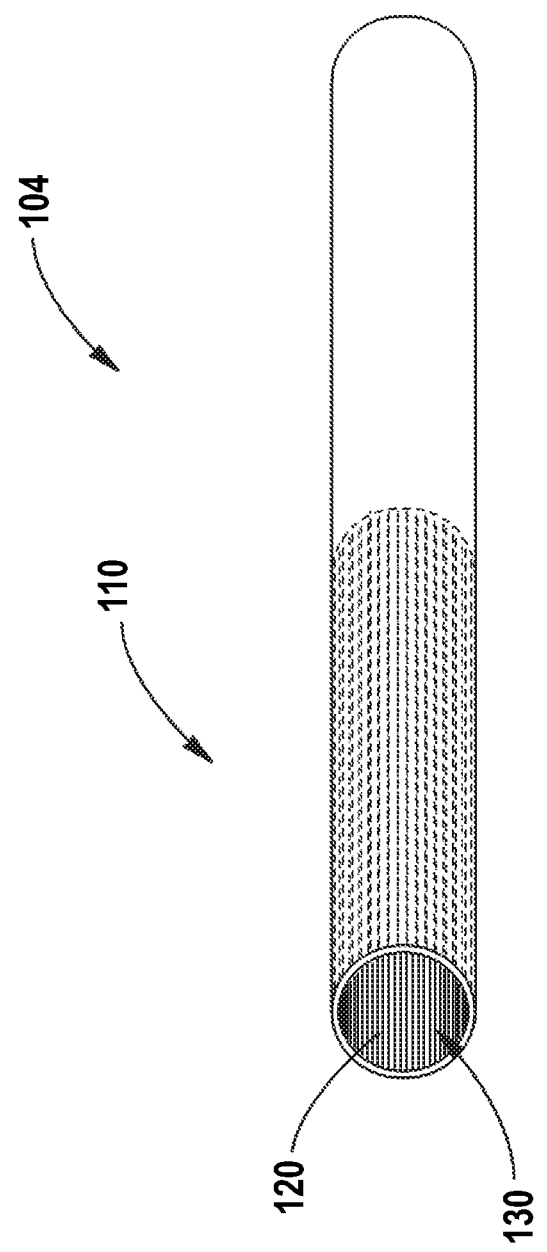
Figure 4:
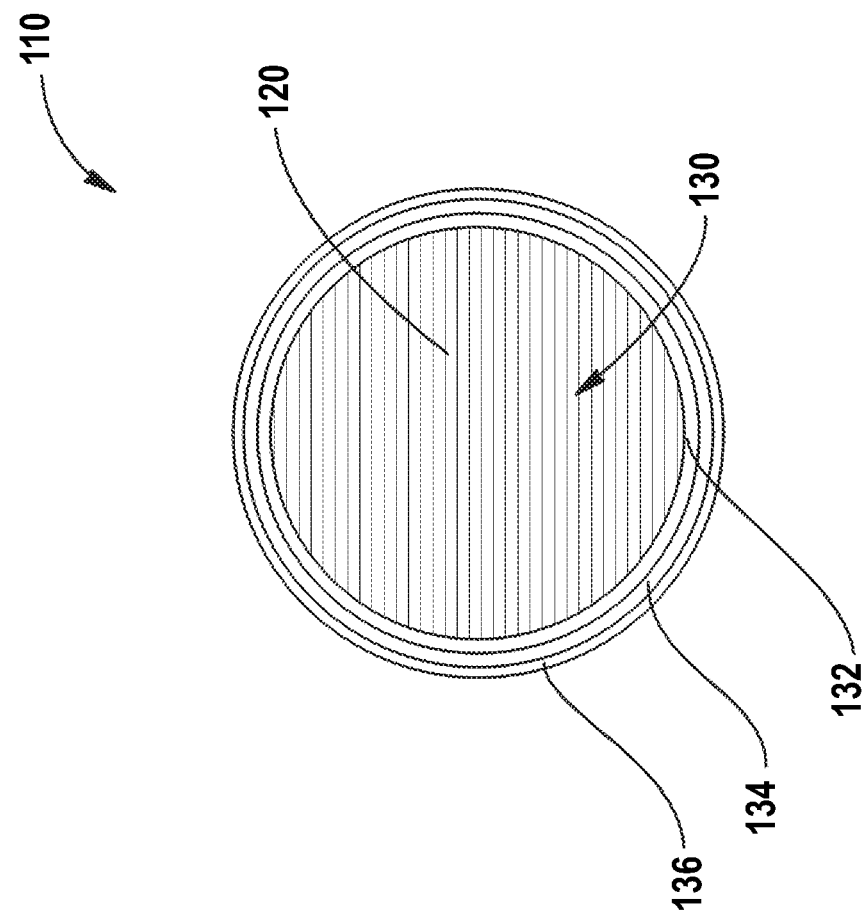
Figure 5:
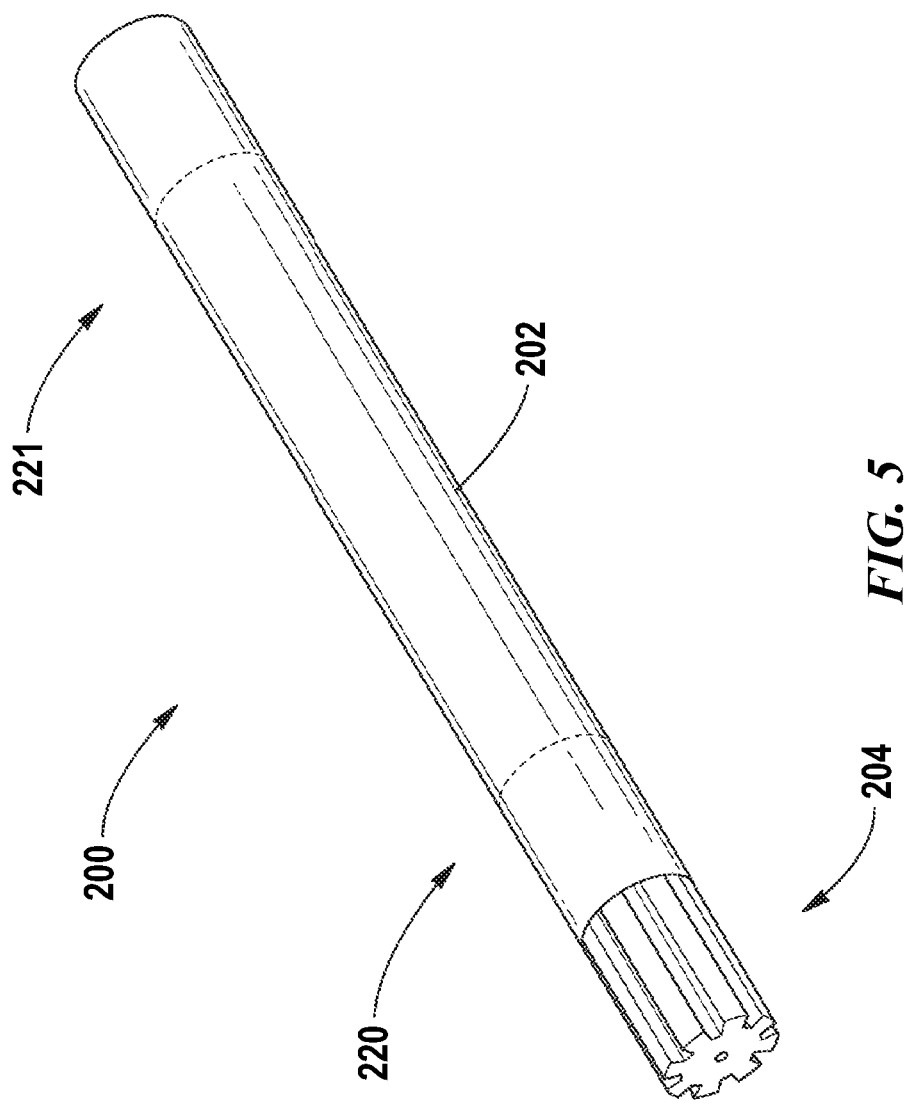
Figure 6:
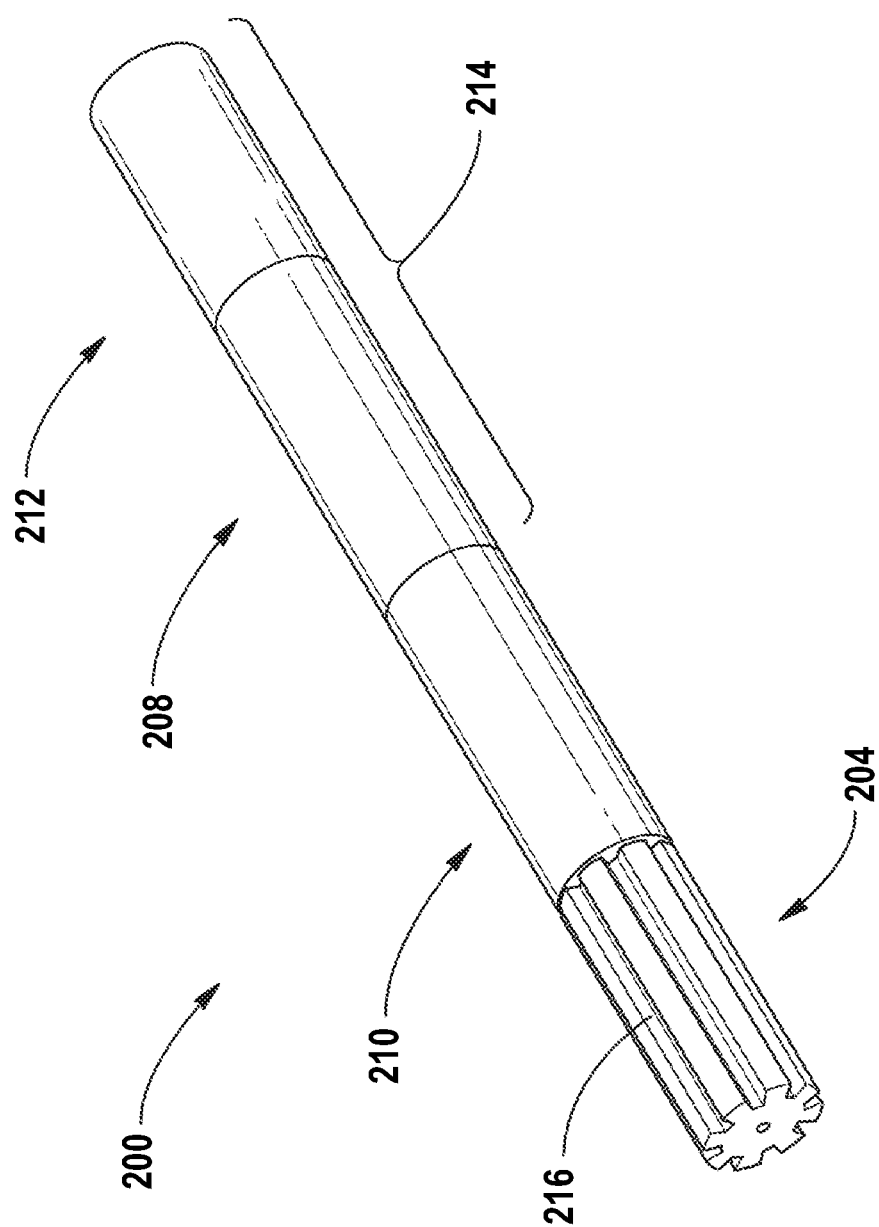

Having thus described aspects of the disclosure in the foregoing general terms, reference will now be made to the accompanying drawings, which are not necessarily drawn to scale, and wherein:

FIG. 1 illustrates a perspective view of an aerosol delivery device comprising a control body and an aerosol source member, wherein the aerosol source member and the control body are coupled to one another, according to an example embodiment of the present disclosure;

FIG. 2 illustrates a perspective view of the aerosol delivery device of FIG. 1 wherein the aerosol source member and the control body are decoupled from one another, according to an example embodiment of the present disclosure;

FIG. 3 illustrates a perspective schematic view of an aerosol source member, according to an example embodiment of the disclosure;

FIG. 4 illustrates a schematic cross-section drawing of a substrate portion of an aerosol source member, according to an example embodiment of the present disclosure;

FIG. 5 illustrates a perspective view of an aerosol source member, according to an example embodiment of the present disclosure; and FIG. 6 illustrates a perspective view of the aerosol source member of FIG. 5 with an outer wrap removed, according to one embodiment of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like. As used herein, "substantially free" refers to concentrations of a given substance of less than 1% by weight or less than 0.5% by weight or less than 0.1% by weight based on total weight of a material.

As described hereinafter, example embodiments of the present disclosure relate to nanocellulose substrates for use in aerosol source members for use with aerosol delivery devices. The use of nanocellulose substrates can increase the absorbency/affinity of the substrate for aerosol precursor materials, which, in turn, can increase loading levels of aerosol precursor material into the substrate. The use of nanocellulose as a component of a substrate material can also serve to add mechanical strength to the substrate, which can improve durability of the substrate material during manufacturing processes.

Some embodiments of aerosol source members according to the present disclosure use electrical energy to heat a material to form an inhalable substance (e.g., electrically heated tobacco products). Other embodiments of aerosol source members according to the present disclosure use an ignitable heat source to heat a material (preferably without combusting the material to any significant degree) to form an inhalable substance (e.g., carbon heated tobacco products). Preferably, the material is heated without combusting the material to any significant degree. Components of such systems have the form of articles that are sufficiently compact to be considered hand-held devices. That is, use of components of preferred aerosol delivery devices does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example embodiments, components of aerosol delivery devices may be characterized as electronic cigarettes, and those electronic cigarettes most preferably incorporate tobacco and/or components derived from tobacco, and hence deliver tobacco derived components in aerosol form.

Aerosol generating components of certain preferred aerosol delivery devices and/or aerosol source members may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol delivery device in accordance with some example embodiments of the present disclosure can hold and use that component much like a smoker employs a traditional type of smoking article, draw on one end of that piece for inhalation of aerosol produced by that piece, take or draw puffs at selected intervals of time, and the like.

While the systems are generally described herein in terms of embodiments associated with aerosol delivery devices and/or aerosol source members such as so-called "e-cigarettes" or "tobacco heating products," it should be understood that the mechanisms, components, features, and methods may be embodied in many different forms and associated with a variety of articles. For example, the description provided herein may be employed in conjunction with embodiments of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of embodiments relating to aerosol delivery devices by way of example only, and may be embodied and used in various other products and methods.

Aerosol delivery devices and/or aerosol source members of the present disclosure may also be characterized as being vapor-producing articles or medicament delivery articles. Thus, such articles or devices may be adapted so as to provide one or more substances (e.g., flavors and/or pharmaceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like. The physical form of the inhalable substance is not necessarily limited by the nature of the inventive devices but rather may depend upon the nature of the medium and the inhalable substance itself as to whether it exists in a vapor state or an aerosol state. In some embodiments, the terms "vapor" and "aerosol" may be interchangeable. Thus, for simplicity, the terms "vapor" and "aerosol" as used to describe aspects of the disclosure are understood to be interchangeable unless stated otherwise.

In some embodiments, aerosol delivery devices of the present disclosure may comprise some combination of a power source (e.g., an electrical power source), at least one control component (e.g., means for actuating, controlling, regulating and ceasing power for heat generation, such as by controlling electrical current flow from the power source to other components of the article—e.g., a microprocessor, individually or as part of a microcontroller), a heating member (e.g., an electrical resistance heating element or other component and/or an inductive coil or other associated components and/or one or more radiant heating elements), and an aerosol source member that includes a substrate portion capable of yielding an aerosol upon application of sufficient heat. Note that it is possible to physically combine one or more of the above-noted components. For instance, in certain embodiments, a conductive heater trace can be printed on the surface of a substrate material as described herein (i.e., a nanocellulose substrate film) using a conductive ink such that the heater trace can be powered by the power source and used as the resistance heating element. Example conductive inks include graphene inks and inks containing various metals, such as inks including silver, gold, palladium, platinum, and alloys or other combinations thereof (e.g., silver-palladium or silver-platinum inks), which can be printed on a surface using processes such as gravure printing, flexographic printing, off-set printing, screen printing, ink-jet printing, or other appropriate printing methods.

In various embodiments, a number of these components may be provided within an outer body or shell, which, in some embodiments, may be referred to as a housing. The overall design of the outer body or shell may vary, and the format or configuration of the outer body that may define the overall size and shape of the aerosol delivery device may vary. Although other configurations are possible, in some embodiments an elongated body resembling the shape of a cigarette or cigar may be a formed from a single, unitary housing or the elongated housing can be formed of two or more separable bodies. For example, an aerosol delivery device may comprise an elongated shell or body that may be substantially tubular in shape and, as such, resemble the shape of a conventional cigarette or cigar. In one example, all of the components of the aerosol delivery device are contained within one housing or body. In other embodiments, an aerosol delivery device may comprise two or more housings that are joined and are separable. For example, an aerosol delivery device may possess at one end a control body comprising a housing containing one or more reusable components (e.g., an accumulator such as a rechargeable battery and/or rechargeable supercapacitor, and various electronics for controlling the operation of that article), and at the other end and removably coupleable thereto, an outer body or shell containing a disposable portion (e.g., a disposable flavor-containing aerosol source member).

In other embodiments, aerosol source members of the present disclosure may generally include an ignitable heat source configured to heat a substrate material. The substrate material and/or at least a portion of the heat source may be covered in an outer wrap, or wrapping, a casing, a component, a module, a member, or the like. The overall design of the enclosure is variable, and the format or configuration of the enclosure that defines the overall size and shape of the aerosol source member is also variable. Although other configurations are possible, it may be desirable, in some aspects, that the overall design, size, and/or shape of these embodiments resemble that of a conventional cigarette or cigar. In various aspects, the heat source may be capable of generating heat to aerosolize a substrate material that comprises, for example, a substrate material associated with an aerosol precursor composition, an extruded structure and/or substrate, tobacco and/or a tobacco related material, such as a material that is found naturally in tobacco that is isolated directly from the tobacco or synthetically prepared, in a solid or liquid form (e.g., beads, sheets, shreds, a wrap), or the like.

More specific formats, configurations and arrangements of various substrate materials, aerosol source members, and components within aerosol delivery devices of the present disclosure will be evident in light of the further disclosure provided hereinafter. Additionally, the selection of various aerosol delivery device components may be appreciated upon consideration of the commercially available electronic aerosol delivery devices. Further, the arrangement of the components within the aerosol delivery device may also be appreciated upon consideration of the commercially available electronic aerosol delivery devices.

In this regard, FIG. 1 illustrates an aerosol delivery device 100 according to an example embodiment of the present disclosure. The aerosol delivery device 100 may include a control body 102 and an aerosol source member 104. In various embodiments, the aerosol source member 104 and the control body 102 may be permanently or detachably aligned in a functioning relationship. In this regard, FIG. 1 illustrates the aerosol delivery device 100 in a coupled configuration, whereas FIG. 2 illustrates the aerosol delivery device 100 in a decoupled configuration. Various mechanisms may connect the aerosol source member 104 to the control body 102 to result in a threaded engagement, a press-fit engagement, an interference fit, a sliding fit, a magnetic engagement, or the like.

In various embodiments, the aerosol delivery device 100 according to the present disclosure may have a variety of overall shapes, including, but not limited to an overall shape that may be defined as being substantially rod-like or substantially tubular shaped or substantially cylindrically shaped. In the embodiments of FIGS. 1-2, the device 100 has a substantially round cross-section; however, other cross-sectional shapes (e.g., oval, square, triangle, etc.) also are encompassed by the present disclosure. For example, in some embodiments one or both of the control body 102 or the aerosol source member 104 (and/or any subcomponents) may have a substantially rectangular shape, such as a substantially rectangular cuboid shape (e.g., similar to a USB flash drive). In other embodiments, one or both of the control body 102 or the aerosol source member 104 (and/or any subcomponents) may have other hand-held shapes. For example, in some embodiments the control body 102 may have a small box shape, various pod mod shapes, or a fob-shape. Thus, such language that is descriptive of the physical shape of the article may also be applied to the individual components thereof, including the control body 102 and the aerosol source member 104.

Alignment of the components within the aerosol delivery device of the present disclosure may vary across various embodiments. In some embodiments, the substrate portion may be positioned proximate a heating member so as to maximize aerosol delivery to the user. Other configurations, however, are not excluded. Generally, the heating member may be positioned sufficiently near the substrate portion so that heat from the heating member can volatilize the substrate portion (as well as, in some embodiments, one or more flavorants, medicaments, or the like that may likewise be provided for delivery to a user) and form an aerosol for delivery to the user. When the heating member heats the substrate portion, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device 100 of various embodiments may incorporate a battery and/or other electrical power source to provide current flow sufficient to provide various functionalities to the aerosol delivery device, such as powering of the heating member, powering of control systems, powering of indicators, and the like. As will be discussed in more detail below, the power source may take on various embodiments. Preferably, the power source may be able to deliver sufficient power to rapidly activate the heating member to provide for aerosol formation and power the aerosol delivery device through use for a desired duration of time. In some embodiments, the power source is sized to fit conveniently within the aerosol delivery device so that the aerosol delivery device can be easily handled. Examples of useful power sources include lithium-ion batteries that are preferably rechargeable (e.g., a rechargeable lithium-manganese dioxide battery). In particular, lithium polymer batteries can be used as such batteries can provide increased safety. Other types of batteries—e.g., N50-AAA CADNICA nickel-cadmium cells—may also be used. Additionally, a preferred power source is of a sufficiently light weight to not detract from a desirable smoking experience. Some examples of possible power sources are described in U.S. Pat. No. 9,484,155 to Peckerar et al., and U.S. Pat. App. Pub. No. 2017/0112191 to Sur et al., filed Oct. 21, 2015, the disclosures of which are incorporated herein by reference in their respective entireties.

In specific embodiments, one or both of the control body 102 and the aerosol source member 104 may be referred to as being disposable or as being reusable. For example, the control body 102 may have a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. Further, in some embodiments, the aerosol source member 104 may comprise a single-use device. A single use component for use with a control body is disclosed in U.S. Pat. No. 8,910,639 to Chang et al., which is incorporated herein by reference in its entirety.

In further embodiments, the power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor.

Further components may be utilized in the aerosol delivery device of the present disclosure. For example, the aerosol delivery device may include a flow sensor that is sensitive either to pressure changes or air flow changes as the consumer draws on the article (e.g., a puff-actuated switch). Other possible current actuation/deactuation mechanisms may include a temperature actuated on/off switch or a lip pressure actuated switch. An example mechanism that can provide such puff-actuation capability includes a Model 163PC01D36 silicon sensor, manufactured by the MicroSwitch division of Honeywell, Inc., Freeport, Ill. Representative flow sensors, current regulating components, and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference is also made to the control schemes described in U.S. Pat. No. 9,423,152 to Ampolini et al., which is incorporated herein by reference in its entirety.

In another example, an aerosol delivery device may comprise a first conductive surface configured to contact a first body part of a user holding the device, and a second conductive surface, conductively isolated from the first conductive surface, configured to contact a second body part of the user. As such, when the aerosol delivery device detects a change in conductivity between the first conductive surface and the second conductive surface, a vaporizer is activated to vaporize a substance so that the vapors may be inhaled by the user holding unit. The first body part and the second body part may be a lip or parts of a hand(s). The two conductive surfaces may also be used to charge a battery contained in the personal vaporizer unit. The two conductive surfaces may also form, or be part of, a connector that may be used to output data stored in a memory. Reference is made to U.S. Pat. No. 9,861,773 to Terry et al., which is incorporated herein by reference in its entirety.

In addition, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties.

Further examples of components related to electronic aerosol delivery articles and disclosing materials or components that may be used in the present device include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. Pat. App. Pub. No. 2017/0099877 to Worm et al., filed Oct. 13, 2015, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various embodiments, and all of the foregoing disclosures are incorporated herein by reference in their entireties.

Referring to FIG. 2, in the depicted embodiment, the aerosol source member 104 comprises a heated end 106, which is configured to be inserted into the control body 102, and a mouth end 108, upon which a user draws to create the aerosol. At least a portion of the heated end 106 may include a substrate portion 110. As will be discussed in more detail below, in various embodiments the substrate portion 110 may comprise a nanocellulose material impregnated with an aerosol precursor composition. In various embodiments, the aerosol source member 104, or a portion thereof, may be wrapped in an exterior overwrap material 112. In various embodiments, the mouth end 108 of the aerosol source member 104 may include a filter 114, which may, for example, be made of a cellulose acetate or polypropylene material. The filter 114 may additionally or alternatively contain strands of tobacco containing material, such as described in U.S. Pat. No. 5,025,814 to Raker et al., which is incorporated herein by reference in its entirety. In various embodiments, the filter 114 may increase the structural integrity of the mouth end of the aerosol source member, and/or provide filtering capacity, if desired, and/or provide resistance to draw. In some embodiments, the filter may comprise discrete segments. For example, some embodiments may include a segment providing filtering, a segment providing draw resistance, a hollow segment providing a space for the aerosol to cool, a segment providing increased structural integrity, other filter segments, and any one or any combination of the above.

In some embodiments, the material of the exterior overwrap 112 may comprise a material that resists transfer of heat, which may include a paper or other fibrous material, such as a cellulose material. The exterior overwrap material may also include at least one filler material imbedded or dispersed within the fibrous material. In various embodiments, the filler material may have the form of water insoluble particles. Additionally, the filler material may incorporate inorganic components. In various embodiments, the exterior overwrap may be formed of multiple layers, such as an underlying, bulk layer and an overlying layer, such as a typical wrapping paper in a cigarette. Such materials may include, for example, lightweight "rag fibers" such as flax, hemp, sisal, rice straw, and/or esparto. The exterior overwrap may also include a material typically used in a filter element of a conventional cigarette, such as cellulose acetate. Further, an excess length of the exterior overwrap at the mouth end 108 of the aerosol source member may function to simply separate the substrate portion 110 from the mouth of a consumer or to provide space for positioning of a filter material, as described below, or to affect draw on the article or to affect flow characteristics of the vapor or aerosol leaving the device during draw. Further discussions relating to the configurations for exterior overwrap materials that may be used with the present disclosure may be found in U.S. Pat. No. 9,078,473 to Worm et al., which is incorporated herein by reference in its entirety.

In various embodiments, other components may exist between the substrate portion 110 and the mouth end 108 of the aerosol source member 104. For example, in some embodiments one or any combination of the following may be positioned between the substrate portion 110 and the mouth end 108 of the aerosol source member 104: an air gap; a hollow tube structure; phase change materials for cooling air; flavor releasing media; ion exchange fibers capable of selective chemical adsorption; aerogel particles as filter medium; and other suitable materials. Some examples of possible phase change materials include, but are not limited to, salts, such as $AgNO_3$, $AlCl_3$, $TaCl_3$, $InCl_3$, $SnCl_2$, $AlI_3$, and $TiI_4$; metals and metal alloys such as selenium, tin, indium, tin-zinc, indium-zinc, or indium-bismuth; and organic compounds such as D-mannitol, succinic acid, p-nitrobenzoic acid, hydroquinone and adipic acid. Other examples are described in U.S. Pat. No. 8,430,106 to Potter et al., which is incorporated herein by reference in its entirety.

As will be discussed in more detail below, the present disclosure is configured for use with a conductive and/or inductive heat source to heat a substrate material to form an aerosol. In various embodiments, a conductive heat source may comprise a heating assembly that comprises a resistive heating member. Resistive heating members may be configured to produce heat when an electrical current is directed therethrough. Electrically conductive materials useful as resistive heating members may be those having low mass, low density, and moderate resistivity and that are thermally stable at the temperatures experienced during use. Useful heating members heat and cool rapidly, and thus provide for the efficient use of energy. Rapid heating of the member may be beneficial to provide almost immediate volatilization of an aerosol precursor material in proximity thereto. Rapid cooling prevents substantial volatilization (and hence waste) of the aerosol precursor material during periods when aerosol formation is not desired. Such heating members may also permit relatively precise control of the temperature range experienced by the aerosol precursor material, especially when time based current control is employed. Useful electrically conductive materials are preferably chemically non-reactive with the materials being heated (e.g., aerosol precursor materials and other inhalable substance materials) so as not to adversely affect the flavor or content of the aerosol or vapor that is produced. Some example, non-limiting, materials that may be used as the electrically conductive material include carbon, graphite, carbon/graphite composites, metals, ceramics such as metallic and non-metallic carbides, nitrides, oxides, silicides, inter-metallic compounds, cermets, metal alloys, and metal foils. In particular, refractory materials may be useful. Various, different materials can be mixed to achieve the desired properties of resistivity, mass, and thermal conductivity. In specific embodiments, metals that can be utilized include, for example, nickel, chromium, alloys of nickel and chromium (e.g., nichrome), and steel. Materials that can be useful for providing resistive heating are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties.

In various embodiments, a heating member may be provided in a variety of forms, such as in the form of a foil, a foam, a mesh, a hollow ball, a half ball, discs, spirals, fibers, wires, films, yarns, strips, ribbons, or cylinders. Such heating members often comprise a metal material and are configured to produce heat as a result of the electrical resistance associated with passing an electrical current therethrough. Such resistive heating members may be positioned in proximity to, and/or in direct contact with, the substrate portion. For example, in one embodiment, a heating member may comprise a cylinder or other heating device located in the control body 102, wherein the cylinder is constructed of one or more conductive materials, including, but not limited to, copper, aluminum, platinum, gold, silver, iron, steel, brass, bronze, carbon (e.g., graphite), or any combination thereof. In various embodiments, the heating member may also be coated with any of these or other conductive materials. The heating member may be located proximate an engagement end of the control body 102, and may be configured to substantially surround a portion of the heated end 106 of the aerosol source member 104 that includes the substrate portion 110. In such a manner, the heating member may be located proximate the substrate portion 110 of the aerosol source member 104 when the aerosol source member is inserted into the control body 102. In other examples, at least a portion of a heating member may penetrate at least a portion of an aerosol source member (such as, for example, one or more prongs and/or spikes that penetrate an aerosol source member), when the aerosol source member is inserted into the control body. Although in some embodiments the heating member may comprise a cylinder, it should be noted that in other embodiments, the heating member may take a variety of forms and, in some embodiments, may make direct contact with and/or penetrate the substrate portion.

As described above, in addition to being configured for use with a conductive heat source, the present disclosure may also be configured for use with an inductive heat source to heat a substrate portion to form an aerosol. In various embodiments, an inductive heat source may comprise a resonant transformer, which may comprise a resonant transmitter and a resonant receiver (e.g., a susceptor). In some embodiments, the resonant transmitter and the resonant receiver may be located in the control body 102. In other embodiments, the resonant receiver, or a portion thereof, may be located in the aerosol source member 104. For example, in some embodiments, the control body 102 may include a resonant transmitter, which, for example, may comprise a foil material, a coil, a cylinder, or other structure configured to generate an oscillating magnetic field, and a resonant receiver, which may comprise one or more prongs that extend into the substrate portion or are surrounded by the substrate portion.

In other embodiments, a resonant transmitter may comprise a helical coil configured to circumscribe a cavity into which an aerosol source member, and in particular, a substrate portion of an aerosol source member, is received. In some embodiments, the helical coil may be located between an outer wall of the device and the receiving cavity. In one embodiment, the coil winds may have a circular cross section shape; however, in other embodiments, the coil winds may have a variety of other cross section shapes, including, but not limited to, oval shaped, rectangular shaped, L-shaped, T-shaped, triangular shaped, and combinations thereof. In another embodiment, a pin may extend into a portion of the receiving cavity, wherein the pin may comprise the resonant transmitter, such as by including a coil structure around or within the pin. In various embodiments, an aerosol source member may be received in the receiving cavity wherein one or more components of the aerosol source member may serve as the resonant receiver. Other possible resonant transformer components, including resonant transmitters and resonant receivers, are described in U.S. patent application Ser. No. 15/799,365, filed on Oct. 31, 2017, and titled *Induction Heated Aerosol Delivery Device*, which is incorporated herein by reference in its entirety.

As noted above, in various embodiments the substrate portion 110 may comprise a nanocellulose material, at least partially formed from nanocellulose fibers, impregnated with an aerosol precursor composition. As used herein, nanocellulose material refers to cellulose materials having at least one average particle size dimension in the range of about 1 nm to about 100 nm. Although larger cellulose material sizes could be used, a reduction in aerosol precursor loading would likely result. As a non-limiting example, a suitable nanocellulose material may be a fibrous material prepared from any variety of cellulose-containing materials, such as wood (e.g., eucalyptus trees), grasses (e.g., bamboo), cotton, tobacco, algae, and other plant-based materials, wherein the fiber is further refined such that a nano-fibrillated cellulose fiber is produced. In various embodiments, the nanocellulose material can contain one or more of tobacco-derived nanocellulose fibers and/or non-tobacco-derived nanocellulose fibers, optionally in combination with one or more additional cellulose materials, such as tobacco-derived cellulosic pulp and/or wood pulp-based cellulose fibers. In some embodiments, the substrate portion 110 may further comprise a hydrophobic additive component, a burn retardant material, a flavorant, and conductive fibers or particles for heat conduction/induction, or any combination thereof. Further, in various embodiments, the form of the substrate portion 110 may include gels, shreds, films, suspensions, extrusions, shavings, capsules, and/or particles (including pellets, beads, strips, or any desired particle shape of varying sizes) and combinations thereof. In some embodiments, the substrate portion 110 may not comprise tobacco. In various other embodiments, the substrate portion 110 may not comprise nicotine. In some embodiments, the substrate portion 110 may further comprise one or more of a non-tobacco-derived nicotine and a flavorant. In certain embodiments, the substrate portion 110 may further comprise one or more pharmaceutical agents. In some embodiments, the substrate portion 110 may further comprise one or more non-tobacco botanicals.

The pharmaceutical agent can be any known agent adapted for therapeutic, prophylactic, or diagnostic use. These can include, for example, synthetic organic compounds, proteins and peptides, polysaccharides and other sugars, lipids, inorganic compounds, and nucleic acid sequences, having therapeutic, prophylactic, or diagnostic activity.

As used herein, the term "botanical material" or "botanical" refers to any plant material or fungal-derived material, including plant material in its natural form and plant material derived from natural plant materials, such as extracts or isolates from plant materials or treated plant materials (e.g., plant materials subjected to heat treatment, fermentation, or other treatment processes capable of altering the chemical nature of the material). For the purposes of the present disclosure, a "botanical material" includes but is not limited to "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any *Nicotiana* species). The botanical materials used in the present invention may comprise, without limitation, any of the compounds and sources set forth herein, including mixtures thereof. Certain botanical materials of this type are sometimes referred to as dietary supplements, nutraceuticals, "phytochemicals" or "functional foods."

Exemplary botanical materials, many of which are associated with antioxidant characteristics, include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, ginseng, gingko biloba, Saint John's Wort, saw palmetto, green tea, black tea, black cohosh, cayenne, chamomile, cloves, cocoa powder, cranberry, dandelion, grapefruit, honeybush, echinacea, garlic, evening primrose, feverfew, ginger, goldenseal, hawthorn, hibiscus flower, jiaogulan, kava, lavender, licorice, marjoram, milk thistle, mints (menthe), oolong tea, beet root, orange, oregano, papaya, pennyroyal, peppermint, red clover, rooibos (red or green), rosehip, rosemary, sage, clary sage, savory, spearmint, spirulina, slippery elm bark, sorghum bran hi-tannin, sorghum grain hi-tannin, sumac bran, comfrey leaf and root, goji berries, gutu kola, thyme, turmeric, uva ursi, valerian, wild yam root, wintergreen, yacon root, yellow dock, yerba mate, yerba santa, bacopa monniera, withania somnifera, Lion's mane, and silybum marianum.

In certain embodiments, the nanocellulose material is admixed with a reconstituted tobacco material, using, for example, various casting and paper-making techniques known in the art. The reconstituted tobacco material can include wood pulp, tobacco fibers, botanicals, or other cellulose components in addition to the nanocellulose material. In some embodiments, the addition of the nanocellulose material to the reconstituted tobacco material can serve to enhance both absorbency and mechanical strength of the resulting material. Reconstituted tobacco materials, and methods of providing such materials, are set forth in U.S. Pat. No. 4,674,519 to Keritsis et al.; U.S. Pat. No. 4,807,809 to Pryor et al.; U.S. Pat. No. 4,889,143 to Pryor et al.; U.S. Pat. No. 4,941,484 to Clapp et al.; U.S. Pat. No. 4,972,854 to Kiernan et al.; U.S. Pat. No. 4,987,906 to Young et al.; U.S. Pat. No. 5,025,814 to Raker; U.S. Pat. No. 5,099,864 to Young et al.; U.S. Pat. No. 5,143,097 to Sohn et al.; U.S. Pat. No. 5,159,942 to Brinkley et al.; U.S. Pat. No. 5,322,076 to Brinkley et al.; U.S. Pat. No. 5,339,838 to Young et al.; U.S. Pat. No. 5,377,698 to Litzinger et al.; U.S. Pat. No. 5,501,237 to Young; and U.S. Pat. No. 6,216,707 to Kumar; each of which is incorporated herein by reference in its entirety.

In one particular embodiment, a tobacco-derived nanocellulose material can be formed by receiving a tobacco pulp in a dilute form such that the tobacco pulp is a tobacco pulp suspension with a consistency of less than about 5%, and mechanically fibrillating the tobacco pulp suspension to generate a tobacco-derived nanocellulose material. The method for generating tobacco pulp generally comprises heating the tobacco material in a strong base to separate the undesired components such as hemicelluloses and lignin present in the tobacco raw material from cellulose, and filtering the resulting mixture to obtain the desired cellulose material with the least amount of impurities. The resulting tobacco pulp can be further modified to produce numerous nanocellulose materials such as cellulose nanofibrils (CNF), cellulose nanocrystals (CNC), and cellulose microfibrils (CMF), differing from each other mainly based on their isolation methods from the tobacco pulp. The nanocellulose materials described herein will typically comprise materials where particles (whether unbound or as part of an aggregate or agglomerate) within a given particle distribution exhibit at least one average particle size dimension in the range of about 1 nm to about 100 nm. Average particle sizes can be determined by review of a select number of particle images using transmission electron microscopy (TEM) and averaging the result. Materials and methods that can be useful for providing tobacco-derived nanocellulose are described in U.S. Pat. No. 10,196,778 to Sebastian et al., which is incorporated herein by reference in its entirety. In some embodiments, nanocellulose materials and conventional wood pulp-based cellulose fibers may be used in combination to form substrate materials.

In some embodiments, the nanocellulose material comprises an apparent viscosity ranging from about 5,000 to about 40,000 mPa*s, preferably from about 20,000 to about 35,000 mPa*s, more preferably from about 20,000 to about 30,000 mPa*s at a consistency of 1.5%. Apparent viscosity is measured at 1.5% fixed consistency with Brookfield rheometer RVDV-III at 10 rpm and using the vane spindles.

In some embodiments, the tensile strength of the nanocellulose substrate material is greater than about 120 Mpa, preferably greater than about 130 Mpa or greater than about 140 Mpa (e.g., ranges from about 140 to about 180 MPa or from about 150 to about 170 Mpa). In some embodiments, the strain of the nanocellulose-based substrate material is at least about 11% or at least about 12%, such as a range from about 10 to about 15%, or from about 11 to about 14%. In some embodiments, the tensile modulus of the nanocellulose-based substrate material is at least about 4 Gpa, such as a range from about 4 to about 6 Gpa. Tensile properties can be measured using a modified SCN P 38:80 Paper and board-Determination of tensile strength-procedure; Vartiainen et al. "Hydrophobization of cellophane and cellulose nanofibrils films by supercritical state carbon dioxide impregnation with walnut oil" Biorefinery, vol. 31 no. (4) 2016, which is hereby incorporated by reference in its entirety. Cross-head speed during test is 2 mm/min and the sample width is 15 mm. Gauge length is 20 mm.

In some embodiments, the oxygen permeability of the nanocellulose-based substrate material is less than 0.2, or less than 0.1, or less than 0.05 cc×mm/m$^2$×day at a temperature of 23° C. and at a relative humidity (RH) of 0%, and less than about 20, or less than about 10, or less than about 5 cc×mm/m$^2$×day at a temperature of 23° C. and at a relative humidity (RH) of 80%. Oxygen permeability can be measured using ASTM D3985; Vartiainen et al. "Hydrophobization of cellophane and cellulose nanofibrils films by supercritical state carbon dioxide impregnation with walnut oil" Biorefinery, vol. 31 no. (4) 2016, which is hereby incorporated by reference in its entirety.

In some embodiments, the substrate portion 110 is loaded with an aerosol precursor composition. In various embodiments, loading of the substrate portion 110 is achieved by impregnating the nanocellulose material with the aerosol precursor composition. In some embodiments, the nanocellulose material is impregnated with an aerosol precursor composition at a loading of at least about 20%, at least about 25%, or at least about 30% by weight, at least about 35% by weight, at least about 40% by weight, at least about 45% by weight, or at least about 50% by weight, based on a total weight of the impregnated material. Example ranges of aerosol precursor material include about 20% to about 60% by weight, such as about 25% to about 50% or about 30% to about 45%, based on the total weight of the impregnated material. Methods for loading aerosol precursor compositions onto substrate portions are described in U.S. Pat. No. 9,974,334 to Dooly et al., and U.S. Pub. Pat. App. Nos. 2015/0313283 to Collett et al. and 2018/0279673 to Sebastian et al., the disclosures of which are incorporated by reference herein in their entirety.

Nanocellulose materials are naturally hydrophilic in nature (although such materials can be inherently hydrophobic when using certain manufacturing processes), and thus exhibit a high degree of absorption of hydrophilic aerosol precursor materials such as glycerin. In certain embodiments, the hydrophobicity of the nanocellulose substrate material can be enhanced in order to improve chemical compatibility of the substrate material with a hydrophobic component of an aerosol precursor material, such as menthol. Enhancing hydrophobicity of a nanocellulose material surface typically involves either physical interaction/adsorption of hydrophobic molecules onto the surface or grafting hydrophobic molecules onto the surface via chemical bonding, or a combination of such techniques. Examples of agents that can be physically adsorbed or otherwise associated with a nanocellulose surface include poly-DADMAC (polydiallyldimethylammonium chloride), cetrimonium bromide, and perfluoro-octadecanoic acid. Examples of chemical modification/grafting agents include acetic anhydride, hexamethyl disilazane, and hydroxyethylmethacrylate. Methylation and silylation are examples of grafting techniques that can increase hydrophobicity of a surface. See, also, the additives set forth in Missoum et al. Nanofibrillated Cellulose surface Modifications: A Review, Materials, 2013, 6, 1745-1766; Dufresne et al, Nanocellulose: a new ageless bio nanomaterial, Materials Today, 16 (6), 2013, 220-227; Peng et al, Chemistry and applications of nanocrystalline cellulose and its derivatives: A nanotechnology perspective, Canadian Journal of Chemical Engineering, 9999, 2011, 1-16; and Wang and Piao, From hydrophilicity to hydrophobicity: a critical review—part II: hydrophobic conversion, Wood and Fiber Science, 43(1), 2011, 41-46.

As noted, in various embodiments, the substrate portion 110 may include an additive component that increases the hydrophobicity of the substrate. In various embodiments, the additive component in the substrate portion 110 is added to the nanocellulose material prior to impregnating the nanocellulose material, such that the additive component chemically or physically modifies the nanocellulose material making it more hydrophobic, further allowing the nanocellulose material to undergo increased loading of hydrophobic aerosol precursor materials, such as menthol. Examples of suitable hydrophobic aerosol precursor compositions for loading onto nanocellulose materials include flavorants selected from the group consisting of esters, terpenes (including cyclic terpenes), aromatics, and lactones. Additional examples of suitable hydrophobic aerosol precursor compositions include, but are not limited to, methyl butyrate, ethyl butyrate, isoamyl acetate, pentyl pentanoate, citral, nerol, limonene, citronella, menthol, carvonce, eugenol, anisol, benzaldehyde, massoia lactone, sotolon, jasmine lactone, gamma-decalactone, geraniol, and delta-decalactone. The hydrophobic component can also be an essential oil (e.g., peppermint oil, orange oil, and the like) or other plant extracts, absolutes or oleoresins (e.g., fenugreek, ginger, and the like).

In certain other embodiments, the substrate portion 110 may be divided into various sub-portions. In some embodiments, one or more of the sub-portions may include an additive component that increases the hydrophobicity of that sub-portion (hereinafter, "treated sub-portion") and one or more of the sub-portions may not include a hydrophobic additive component (hereinafter, "untreated sub-portion"). Advantageously, this allows for one or more untreated sub-portions that comprise hydrophilic nanocellulose materials and one or more treated sub-portions that comprise hydrophobic nanocellulose materials. In some embodiments, the untreated sub-portions may be positioned closer to the heat source as compared to the treated sub-portions so as to facilitate more heat to the untreated sub-portions. In certain other embodiments, the substrate portion 110 may comprise a segmented configuration of treated and untreated sub-portions, such that the sub-portions are intimately arranged in an end to end configuration. Such configurations allow for a gradient substrate wherein the hydrophobicity of each sub-portion increases the farther in proximity the sub-portion is from the heat source. Generally, sub-portions with higher hydrophobicity concentrations, require lower amounts of heat in order to release the aerosol precursor compositions within the sub-portions. In various embodiments, treated sub-portions and untreated sub-portions may be shredded and dispersed among each other such that the substrate portion 110 comprises a co-mingling of treated sub-portions and untreated sub-portions in a shredded form.

As noted, the substrate portion 110 may also include a burn retardant material. One example of such a material is ammonium phosphate. In some embodiments, other flame/burn retardant materials and additives may be included within the substrate portion 110 and may include organophosphorus compounds, borax, hydrated alumina, graphite, potassium, silica, tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides may also be used. In each aspect of flame-retardant, burn-retardant, and/or scorch-retardant materials used in the substrate material and/or other components (whether alone or in combination with each other and/or other materials), the desirable properties are independent of and resistant to undesirable off-gassing or melting-type behavior. Various manners and methods for incorporating tobacco into smoking articles, and particularly smoking articles that are designed so as to not purposefully burn virtually all of the tobacco within those smoking articles are set forth in U.S. Pat. No. 4,947,874 to Brooks et al.; U.S. Pat. No. 7,647,932 to Cantrell et al.; U.S. Pat. No. 8,079,371 to Robinson et al.; U.S. Pat. No. 7,290,549 to Banerjee et al.; and U.S. Pat. App. Pub. No. 2007/0215167 to Crooks et al.; the disclosures of which are incorporated herein by reference in their entireties.

As noted, the substrate portion 110 may be impregnated with an aerosol precursor composition. In some embodiments, the aerosol precursor composition may comprise glycerin or propylene glycol. Preferred aerosol forming materials include polyhydric alcohols (e.g., glycerin, propylene glycol, and triethylene glycol) and/or water, and any other materials which yield a visible aerosol, as well as any combinations thereof. Representative types of aerosol forming materials are set forth in U.S. Pat. No. 4,793,365 to Sensabaugh, Jr. et al.; and U.S. Pat. No. 5,101,839 to Jakob et al.; PCT Pat. App. Pub. No. WO 98/57556 to Biggs et al.; and *Chemical and Biological Studies on New Cigarette Prototypes that Heat Instead of Burn Tobacco*, R. J. Reynolds Tobacco Company Monograph (1988); which are incorporated herein by reference in their entirety. Other representative types of aerosol precursor components and formulations are also set forth and characterized in U.S. Pat. No. 7,726,320 to Robinson et al., U.S. Pat. No. 8,881,737 to Collett et al., and U.S. Pat. No. 9,254,002 to Chong et al.; and U.S. Pat. Pub. Nos. 2013/0008457 to Zheng et al.; 2015/0020823 to Lipowicz et al.; and 2015/0020830 to Koller, as well as WO 2014/182736 to Bowen et al, the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by British American Tobacco. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN. Embodiments of effervescent materials can be used with the aerosol precursor composition, and are described, by way of example, in U.S. Pat. App. Pub. No. 2012/0055494 to Hunt et al., which is incorporated herein by reference in its entirety. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al; U.S. Pat. No. 8,627,828 to Strickland et al.; and U.S. Pat. No. 9,307,787 to Sun et al.; as well as U.S. Pat. App. Pub. No. 2010/0018539 to Brinkley et al. and PCT WO 97/06786 to Johnson et al., all of which are incorporated by reference herein in their entireties. Additional description with respect to embodiments of aerosol precursor compositions, including description of tobacco or components derived from tobacco included therein, is provided in U.S. Pat. App. Pub. Nos. 2018/0020722 and 2018/0020723, each to Davis et al., which are incorporated herein by reference in their entireties.

As noted, the substrate portion 110 may also include a flavorant. As used herein, reference to a "flavorant" refers to compounds or components that can be aerosolized and delivered to a user and which impart a sensory experience in terms of taste and/or aroma. Some examples of flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Some examples of plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components is variable based upon factors such as the sensory characteristics that are desired for the smoking article, their affinity for the substrate material, their solubilities, and other physiochemical properties. The present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

As noted, the substrate portion 110 may also include conductive fibers or particles for heat conduction or heating by induction. In some embodiments, the conductive fibers or particles may be arranged in a substantially linear and parallel pattern. In some embodiments, the conductive fibers or particles may have a substantially random arrangement. In some embodiments, the conductive fibers or particles may be constructed of or more of an aluminum material, a stainless steel material, a copper material, a carbon material, and a graphite material. In some embodiments, one or more conductive fibers or particles with different Curie temperatures may be included in the substrate material to facilitate heating by induction at varying temperatures.

In one particular embodiment, the substrate portion 110 may comprise a series of overlapping layers of a composite substrate sheet that comprises a nanocellulose material as described herein. A layer of nanocellulose fibers can be formed by any suitable method, such as wet-laid methods and dry-laid methods (e.g., carding or air-laid methods). The resulting layer of nanocellulose fibers can be in the form of a film or a sheet. If desired, an additive component may be used, such as additive components that typically allow cellulose-based fiber sheets to undergo a chemical modification to increase hydrophobicity. In various embodiments, the nanocellulose film or sheet may be impregnated with an aerosol precursor composition and/or additional flavorants. The nanocellulose sheet or film may be formed without the use of a polymeric binder as is typically required when forming cohesive sheet materials. Typical polymeric binders that can be avoided in certain embodiments of the invention include, but are not limited to, alginates, celluloses (e.g., methyl cellulose, ethyl cellulose, ethyl hydroxyethyl cellulose, or carboxy methyl cellulose), dextrans, natural gums and derivatives thereof, pectins, and starches. Advantageously, nanocellulose materials, alone, can act as the binder in a nanocellulose sheet or film. Accordingly, in certain advantageous embodiments, a sheet material comprising the nanocellulose material is formed using a casting or papermaking process and the sheet material incorporates one or more aerosol-forming materials and, optionally, one or more flavorants. However, the sheet material can be substantially free or completely free of polymeric binder (e.g., less than 1% by weight or less than 0.5% by weight or less than 0.1% by weight polymeric binder based on total weight of the sheet). In other embodiments, the sheet material can include a polymeric binder to supplement the binding properties of the nanocellulose material.

In one particular embodiment, a substrate sheet according to the present disclosure can be formed by agitating a nano-fibrillated cellulose suspension in a high shear mixture and casting the suspension onto a moving plastic support web. The plastic support web may be pre-treated using a plasma device with a predetermined power level. The nano-fibrillated cellulose suspensions are agitated before film making in a high shear mixer, and after 60 minutes of mixing, an additive is added to the mixing vessel and mixing is continued for another 60 minutes. In various embodiments, the mixing additive may be glycerol, propylene glycol, one or more flavorants, other aerosol precursors, and combinations thereof. After mixing, air may be removed from the nano-fibrillated cellulose suspension by mixing for 5 minutes in a vacuum. After such further mixing, the required amount of nano-fibrillated cellulose suspension for film making is cast on the plastic support web to form a film. The formed nanocellulose films may be allowed to dry in ambient conditions for a required time and then detached from the plastic support web. Optionally, the nanocellulose films may be smoothed using pressing or calendaring methods.

The nanocellulose film or layer may further be coated with a coating. In some embodiments, the coating may include one or more of the following ingredients: a binder, a flame/burn retardant material, an aerosol precursor composition, and a flavorant.

In some embodiments, flame/burn retardant materials and additives may be included within the coating and may include organo-phosphorus compounds, borax, hydrated alumina, graphite, potassium tripolyphosphate, dipentaerythritol, pentaerythritol, and polyols. Others such as nitrogenous phosphonic acid salts, mono-ammonium phosphate, ammonium polyphosphate, ammonium bromide, ammonium borate, ethanolammonium borate, ammonium sulphamate, halogenated organic compounds, thiourea, and antimony oxides are may also be used. In each aspect of flame-retardant, burn-retardant, and/or scorch-retardant materials used in the coating and/or coatings (whether alone or in combination with each other and/or other materials), the desirable properties are preferably provided without undesirable off-gassing, chemically reactive, or melting-type behavior. Additional flavorants, flavoring agents, additives, and other possible enhancing constituents are described in U.S. patent application Ser. No. 15/707,461 to Phillips et al., which is incorporated herein by reference in its entirety.

As noted, in various embodiments the coating may include a binder material. Preferred binder materials include alginates, such as ammonium alginate, propylene glycol alginate, potassium alginate, and sodium alginate. Alginates, and particularly high viscosity alginates, may be employed in conjunction with controlled levels of free calcium ions. Other suitable binder materials include hydroxypropylcellulose such as Klucel H from Aqualon Co.; hydroxypropylmethylcellulose such as Methocel K4MS from The Dow Chemical Co.; hydroxyethylcellulose such as Natrosol 250 MRCS from Aqualon Co.; microcrystalline cellulose such as Avicel from FMC; methylcellulose such as Methocel A4M from The Dow Chemical Co.; and sodium carboxymethylcellulose such as CMC 7HF and CMC 7H4F from Hercules Inc. Still other possible binder materials include starches (e.g., corn starch), guar gum, carrageenan, locust bean gum, pectins and xanthan gum. In some embodiments, combinations or blends of two or more binder materials may be employed. Other examples of binder materials are described, for example, in U.S. Pat. No. 5,101,839 to Jakob et al.; and U.S. Pat. No. 4,924,887 to Raker et al., each of which is incorporated herein by reference in its entirety. In some embodiments, the aerosol forming material may be provided as a portion of the binder material (e.g., propylene glycol alginate). In addition, in some embodiments, the binder material may comprise nanocellulose derived from a tobacco or other biomass. In some other embodiments, the binder may include a cyclodextrin.

As such, in various embodiments a coated composite substrate sheet may be created that comprises the nanocellulose material. In various embodiments, one or more composite substrate sheets may be used as a substrate portion, which may be part of an aerosol source member. FIG. 3 illustrates a perspective schematic view of an aerosol source member, according to an example embodiment of the disclosure. In particular, FIG. 3 illustrates the aerosol source member 104 having a substrate portion 110 that comprises a series of overlapping layers 130 of the composite substrate sheet 120. With reference to the description above, in the depicted embodiment, the composite substrate sheet 120 comprises a nanocellulose film or layer at least partially formed from nanocellulose fibers. In various embodiments, the term "overlapping layers" may also include bunched, crumpled, crimped, and/or otherwise gathered layers in which the individual layers may not be obvious.

While in some embodiments the substrate portion may merely comprise overlapping layers of the composite substrate sheet, in other embodiments at least a portion of the overlapping layers may be covered with one or more cover layers. For example, FIG. 4 illustrates a schematic cross-section drawing of a substrate portion of an aerosol source member, according to an example embodiment of the present disclosure. In particular, FIG. 4 illustrates the substrate portion 110, which comprises a series of overlapping layers 130 of the composite substrate sheet 120. In the depicted embodiment, at least a portion of the overlapping layers 130 is substantially surrounded about its outer surface with a first cover layer 132. Although in various embodiments the composition of the first cover layer 132 may vary, in the depicted embodiment the first cover layer 132 comprises a combination of a fibrous material, an aerosol precursor composition, and a binder material. Reference is made to the discussions above relating possible aerosol precursor compositions and binder materials.

In various implementations, the fibrous material may comprise a milled tobacco material. Tobacco materials that may be useful in the present disclosure can vary and may include, for example, flue-cured tobacco, burley tobacco, Oriental tobacco or Maryland tobacco, dark tobacco, dark-fired tobacco and *rustica* tobaccos, as well as other rare or specialty tobaccos, or blends thereof. Tobacco materials also can include so-called "blended" forms and processed forms, such as processed tobacco stems (e.g., cut-rolled or cut-puffed stems), volume expanded tobacco (e.g., puffed tobacco, such as dry ice expanded tobacco (DIET), preferably in cut filler form), reconstituted tobaccos (e.g., reconstituted tobaccos manufactured using paper-making type or cast sheet type processes). Various representative tobacco types, processed types of tobaccos, and types of tobacco blends are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,159,942 to Brinkley et al.; U.S. Pat. No. 5,220,930 to Gentry; U.S. Pat. No. 5,360,023 to Blakley et al.; U.S. Pat. No. 6,701,936 to Shafer et al.; U.S. Pat. No. 7,011,096 to Li et al.; and U.S. Pat. No. 7,017,585 to Li et al.; U.S. Pat. No. 7,025,066 to Lawson et al.; U.S. Pat. App. Pub. No. 2004-0255965 to Perfetti et al.; PCT Pat. App. Pub. No. WO 02/37990 to Bereman; and Bombick et al., Fund. Appl. Toxicol., 39, p. 11-17 (1997); which are incorporated herein by reference in their entireties. Further examples of tobacco compositions that may be useful are disclosed in U.S. Pat. No. 7,726,320 to Robinson et al., which is incorporated herein by reference in its entirety. In some implementations, the milled tobacco material may comprise a blend of flavorful and aromatic tobaccos. In another implementation, the tobacco material may comprise a reconstituted tobacco material, such as described in U.S. Pat. No. 4,807,809 to Pryor et al.; U.S. Pat. No. 4,889,143 to Pryor et al. and U.S. Pat. No. 5,025,814 to Raker, the disclosures of which are incorporated herein by reference in their entirety. Additionally, a reconstituted tobacco material may include a reconstituted tobacco paper for the type of cigarettes described in Chemical and Biological Studies on New Cigarette Prototypes that Heat Instead of Burn Tobacco, R. J. Reynolds Tobacco Company Monograph (1988), the contents of which are incorporated herein by reference in its entirety.

In some implementations, the fibrous material may comprise a plant-derived non-tobacco material, including, but not limited to, hemp, flax, sisal, rice straw, esparto, and/or a cellulose pulp material. In various other implementations, the fibrous material may comprise reconstituted tobacco by itself or combined with other fibrous materials. Some example manners and methods for providing a reconstituted tobacco sheet, including casting and paper-making techniques, are set forth in U.S. Pat. No. 4,674,519 to Keritsis et al.; U.S. Pat. No. 4,941,484 to Clapp et al.; U.S. Pat. No. 4,987,906 to Young et al.; U.S. Pat. No. 4,972,854 to Kiernan et al.; U.S. Pat. No. 5,099,864 to Young et al.; U.S. Pat. No. 5,143,097 to Sohn et al.; U.S. Pat. No. 5,159,942 to Brinkley et al.; U.S. Pat. No. 5,322,076 to Brinkley et al.; U.S. Pat. No. 5,339,838 to Young et al.; U.S. Pat. No. 5,377,698 to Litzinger et al.; U.S. Pat. No. 5,501,237 to Young; and U.S. Pat. No. 6,216,707 to Kumar; each of which is incorporated herein by reference in its entirety. In some instances, processed tobaccos, such as certain types of reconstituted tobaccos, can be employed as longitudinally extending strands. See, for example, the type of configuration set forth in U.S. Pat. No. 5,025,814 to Raker, which is incorporated herein by reference in its entirety. In addition, certain types of reconstituted tobacco sheets can be formed, rolled, or gathered into a desired configuration. In still other implementations, the fibrous material may comprise inorganic fibers of various types (e.g., fiber glass, metal wires/screens, etc.) and/or (organic) synthetic polymers. In various implementations, these "fibrous" materials could be unstructured (e.g., randomly distributed like the cellulose fibers in tobacco cast sheet) or structured (e.g., a wire mesh).

In various embodiments, the first cover layer 132 may be constructed via a casting process, such as that described in U.S. Pat. No. 5,697,385 to Seymour et al., the disclosure of which is incorporated herein by reference in its entirety. For example, in some embodiments the fibrous material, aerosol precursor composition, and binder may be blended together to form a slurry, which may be cast onto a surface (such as, for example, a moving belt). The cast slurry may then experience one or more drying and/or doctoring steps such that the result is a relatively consistent thickness cast sheet. Other examples of casting and paper-making techniques are set forth in U.S. Pat. No. 4,674,519 to Keritsis et al.; U.S. Pat. No. 4,941,484 to Clapp et al.; U.S. Pat. No. 4,987,906 to Young et al.; U.S. Pat. No. 4,972,854 to Kiernan et al.; U.S. Pat. No. 5,099,864 to Young et al.; U.S. Pat. No. 5,143,097 to Sohn et al.; U.S. Pat. No. 5,159,942 to Brinkley et al.; U.S. Pat. No. 5,322,076 to Brinkley et al.; U.S. Pat. No. 5,339,838 to Young et al.; U.S. Pat. No. 5,377,698 to Litzinger et al.; U.S. Pat. No. 5,501,237 to Young; and U.S. Pat. No. 6,216,706 to Kumar; the disclosures of which is incorporated herein by reference in their entireties.

In the depicted embodiment, at least a portion of the overlapping layers 130 and the first cover layer 132 are substantially surrounded about an outer surface with a second cover layer 134. Although the composition of the second cover layer 134 may vary, in the depicted embodiment the second cover layer 134 comprises a metal foil material, such as an aluminum foil material. In other embodiments, the second cover layer may comprise other materials, including, but not limited to, a copper material, a tin material, a gold material, an alloy material, a ceramic material, or other thermally conductive amorphous carbon-based material, and/or any combinations thereof. The depicted embodiment further includes a third cover layer 136, which substantially surrounds the overlapping layers 130, first cover layer 132, and the second cover layer 134, about an outer surface thereof. In the depicted embodiment, the third cover layer 136 comprises a paper material, such as a conventional cigarette wrapping paper. In various embodiments, the paper material may comprise rag fibers, such as non-wood plant fibers, and may include flax, hemp, sisal, rice straw, and/or esparto fibers.

Although in some embodiments an aerosol source member and a control body may be provided together as a complete smoking article or pharmaceutical delivery article generally, the components may be provided separately. For example, the present disclosure also encompasses a disposable unit for use with a reusable smoking article or a reusable pharmaceutical delivery article. In specific embodiments, such a disposable unit (which may be an aerosol source member as illustrated in the appended figures) can comprise a substantially tubular shaped body having a heated end configured to engage the reusable smoking article or pharmaceutical delivery article, an opposing mouth end configured to allow passage of an inhalable substance to a consumer, and a wall with an outer surface and an inner surface that defines an interior space. Various embodiments of an aerosol source member (or cartridge) are described in U.S. Pat. No. 9,078,473 to Worm et al., which is incorporated herein by reference in its entirety.

Although some figures described herein illustrate the control body and aerosol source member in a working relationship, it is understood that the control body and the aerosol source member may exist as individual devices. Accordingly, any discussion otherwise provided herein in relation to the components in combination also should be understood as applying to the control body and the aerosol source member as individual and separate components.

In another aspect, the present disclosure may be directed to kits that provide a variety of components as described herein. For example, a kit may comprise a control body with one or more aerosol source members. A kit may further comprise a control body with one or more charging components. A kit may further comprise a control body with one or more batteries. A kit may further comprise a control body with one or more aerosol source members and one or more charging components and/or one or more batteries. In further embodiments, a kit may comprise a plurality of aerosol source members. A kit may further comprise a plurality of aerosol source members and one or more batteries and/or one or more charging components. In the above embodiments, the aerosol source members or the control bodies may be provided with a heating member inclusive thereto. The inventive kits may further include a case (or other packaging, carrying, or storage component) that accommodates one or more of the further kit components. The case could be a reusable hard or soft container. Further, the case could be simply a box or other packaging structure.

FIG. 5 illustrates a perspective view of an aerosol source member, according to another example embodiment of the present disclosure, and FIG. 6 illustrates a perspective view of the aerosol source member of FIG. 5 with an outer wrap removed. In particular, FIG. 5 illustrates an aerosol source member 200 that includes an outer wrap 202, and FIG. 6 illustrates the aerosol source member 200 wherein the outer wrap 202 is removed to reveal the other components of the aerosol source member 200. In the depicted embodiment, the aerosol source member 200 of the depicted embodiment includes a heat source 204, a substrate portion 210, an intermediate component 208, and a filter 212. In the depicted embodiment, the intermediate component 208 and the filter 212 together comprise a mouthpiece 214.

Although an aerosol deliver device and/or an aerosol source member according to the present disclosure may take on a variety of embodiments, as discussed in detail below, the use of the aerosol delivery device and/or aerosol source member by a consumer will be similar in scope. The foregoing description of use of the aerosol delivery device and/or aerosol source member is applicable to the various embodiments described through minor modifications, which are apparent to the person of skill in the art in light of the further disclosure provided herein. The description of use, however, is not intended to limit the use of the articles of the present disclosure but is provided to comply with all necessary requirements of disclosure herein.

In various embodiments, the heat source 204 may be configured to generate heat upon ignition thereof. In the depicted embodiment, the heat source 204 comprises a combustible fuel element that has a generally cylindrical shape and that incorporates a combustible carbonaceous material. In other embodiments, the heat source 204 may have a different shape, for example, a prism shape having a triangular, cubic or hexagonal cross-section. Carbonaceous materials generally have a high carbon content. Preferred carbonaceous materials may be composed predominately of carbon, and/or typically may have carbon contents of greater than about 60 percent, generally greater than about 70 percent, often greater than about 80 percent, and frequently greater than about 90 percent, on a dry weight basis.

In some instances, the heat source 204 may incorporate elements other than combustible carbonaceous materials (e.g., tobacco components, such as powdered tobaccos or tobacco extracts; flavoring agents; salts, such as sodium chloride, potassium chloride and sodium carbonate; heat stable graphite fibers; iron oxide powder; glass filaments; powdered calcium carbonate; alumina granules; ammonia sources, such as ammonia salts; and/or binding agents, such as guar gum, ammonium alginate and sodium alginate). Although specific dimensions of an applicable heat source may vary, in some embodiments, the heat source 204 may have a length in an inclusive range of approximately 7 mm to approximately 20 mm, and in some embodiments may be approximately 17 mm, and an overall diameter in an inclusive range of approximately 3 mm to approximately 8 mm, and in some embodiments may be approximately 4.8 mm (and in some embodiments, approximately 7 mm). Although in other embodiments, the heat source may be constructed in a variety of ways, in the depicted embodiment, the heat source 204 is extruded or compounded using a ground or powdered carbonaceous material, and has a density that is greater than about 0.5 $g/cm^3$, often greater than about 0.7 $g/cm^3$, and frequently greater than about 1 $g/cm^3$, on a dry weight basis. See, for example, the types of fuel source components, formulations and designs set forth in U.S. Pat. No. 5,551,451 to Riggs et al. and U.S. Pat. No. 7,836,897 to Borschke et al., which are incorporated herein by reference in their entireties. Although in various embodiments, the heat source may have a variety of forms, including, for example, a substantially solid cylindrical shape or a hollow cylindrical (e.g., tube) shape, the heat source 204 of the depicted embodiment comprises an extruded monolithic carbonaceous material that has a generally cylindrical shape but with a plurality of grooves 216 extending longitudinally from a first end of the extruded monolithic carbonaceous material to an opposing second end of the extruded monolithic carbonaceous material. In some embodiments, the aerosol delivery device, and in particular, the heat source, may include a heat transfer component. In various embodiments, a heat transfer component may be proximate the heat source, and, in some embodiments, a heat transfer component may be located in or within the heat source. Some examples of heat transfer components are described in in U.S. patent application Ser. No. 15/923,735, filed on Mar. 16, 2018, and titled *Smoking Article with Heat Transfer Component*, which is incorporated herein by reference in its entirety.

Although in the depicted embodiment, the grooves 216 of the heat source 204 are substantially equal in width and depth and are substantially equally distributed about a circumference of the heat source 204, other embodiments may include as few as two grooves, and still other embodiments may include as few as a single groove. Still other embodiments may include no grooves at all. Additional embodiments may include multiple grooves that may be of unequal width and/or depth, and which may be unequally spaced around a circumference of the heat source. In still other embodiments, the heat source may include flutes and/or slits extending longitudinally from a first end of the extruded monolithic carbonaceous material to an opposing second end thereof. In some embodiments, the heat source may comprise a foamed carbon monolith formed in a foam process of the type disclosed in U.S. Pat. No. 7,615,184 to Lobovsky, which is incorporated herein by reference in its entirety. As such, some embodiments may provide advantages with regard to reduced time taken to ignite the heat source. In some other embodiments, the heat source may be co-extruded with a layer of insulation (not shown), thereby reducing manufacturing time and expense. Other embodiments of fuel elements include carbon fibers of the type described in U.S. Pat. No. 4,922,901 to Brooks et al. or other heat source embodiments such as is disclosed in U.S. Pat. App. Pub. No. 2009/0044818 to Takeuchi et al., each of which is incorporated herein by reference in its entirety.

Generally, the heat source is positioned sufficiently near an aerosol delivery component (e.g., a substrate portion) having one or more aerosolizable components so that the aerosol formed/volatilized by the application of heat from the heat source to the aerosolizable components (as well as any flavorants, medicaments, and/or the like that are likewise provided for delivery to a user) is deliverable to the user by way of the mouthpiece. That is, when the heat source heats the substrate portion, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof. Additionally, the selection of various aerosol delivery device elements are appreciated upon consideration of commercially available electronic aerosol delivery devices, such as those representative products listed in the background art section of the present disclosure.

Referring back to FIGS. 5 and 6, the outer wrap 202 may be provided to engage or otherwise join together at least a portion of the heat source 204 with the substrate portion 210 and at least a portion of the mouthpiece 214. In various embodiments, the outer wrap 202 is configured to be retained in a wrapped position in any manner of ways including via an adhesive, or a fastener, and the like, to allow the outer wrap 202 to remain in the wrapped position. Otherwise, in some other aspects, the outer wrap 202 may be configured to be removable as desired. For example, upon retaining the outer wrap 202 in a wrapped position, the outer wrap 202 may be able to be removed from the heat source 204, the substrate portion 210, and/or the mouthpiece 214.

In some embodiments, in addition to the outer wrap 202, the aerosol delivery device may also include a liner that is configured to circumscribe the substrate portion 210 and at least a portion of the heat source 204. Although in other embodiments the liner may circumscribe only a portion of the length of the substrate portion 210, in some embodiments, the liner may circumscribe substantially the full length of the substrate portion 210. In some embodiments, the outer wrap material 202 may include the liner. As such, in some embodiments the outer wrap material 202 and the liner may be separate materials that are provided together (e.g., bonded, fused, or otherwise joined together as a laminate). In other embodiments, the outer wrap 202 and the liner may be the same material. In any event, the liner may be configured to thermally regulate conduction of the heat generated by the ignited heat source 204, radially outward of the liner. As such, in some embodiments, the liner may be constructed of a metal foil material, an alloy material, a ceramic material, or other thermally conductive amorphous carbon-based material, and/or an aluminum material, and in some embodiments may comprise a laminate. In some embodiments, depending on the material of the outer wrap 202 and/or the liner, a thin layer of insulation may be provided radially outward of the liner. Thus, the liner may advantageously provide, in some aspects, a manner of engaging two or more separate components of the aerosol source member 200 (such as, for example, the heat source 204, the substrate portion 210, and/or a portion of the mouthpiece 214), while also providing a manner of facilitating heat transfer axially therealong, but restricting radially outward heat conduction.

As shown in FIG. 5, the outer wrap 202 (and, as necessary, the liner, and the substrate portion 210) may also include one or more openings formed therethrough that allow the entry of air upon a draw on the mouthpiece 214. In various embodiments, the size and number of these openings may vary based on particular design requirements. In the depicted embodiment, a plurality of openings 220 are located proximate an end of the substrate portion 210 closest to the heat source 204, and a plurality of separate cooling openings 221 are formed in the outer wrap 202 (and, in some embodiments, the liner) in an area proximate the filter 212 of the mouthpiece 214. Although other embodiments may differ, in the depicted embodiment, the openings 220 comprise a plurality openings substantially evenly spaced about the outer surface of the aerosol source member 200, and the openings 221 also comprise a plurality of openings substantially evenly spaced around the outer surface of the aerosol source member 200. Although in various embodiments the plurality of openings may be formed through the outer wrap 202 (and, in some embodiments, the liner) in a variety of ways, in the depicted embodiment, the plurality of openings 220 and the plurality of separate cooling openings 221 are formed via laser perforation.

Referring back to FIG. 6, the aerosol source member 200 of the depicted implementation also includes an intermediate component 208 and at least one filter 212. It should be noted that in various implementations, the intermediate component 208 or the filter 212, individually or together, may be considered a mouthpiece 214 of the aerosol source member 200. Although in various implementations, neither the intermediate component nor the filter need be included, in the depicted implementation the intermediate component 208 comprises a substantially rigid member that is substantially inflexible along its longitudinal axis. In the depicted implementation, the intermediate component 208 comprises a hollow tube structure, and is included to add structural integrity to the aerosol source member 200 and provide for cooling the produced aerosol. In some implementations, the intermediate component 208 may be used as a container for collecting the aerosol. In various implementations, such a component may be constructed from any of a variety of materials and may include one or more adhesives. Example materials include, but are not limited to, paper, paper layers, paperboard, plastic, cardboard, and/or composite materials. In the depicted implementation, the intermediate component 208 comprises a hollow cylindrical element constructed of a paper or plastic material (such as, for example, ethyl vinyl acetate (EVA), or other polymeric materials such as poly ethylene, polyester, silicone, etc. or ceramics (e.g., silicon carbide, alumina, etc.), or other acetate fibers), and the filter comprises a packed rod or cylindrical disc constructed of a gas permeable material (such as, for example, cellulose acetate or fibers such as paper or rayon, or polyester fibers).

As noted, in some implementations the mouthpiece 214 may comprise a filter 212 configured to receive the aerosol therethrough in response to the draw applied to the mouthpiece 214. In various implementations, the filter 212 is provided, in some aspects, as a circular disc radially and/or longitudinally disposed proximate the second end of the intermediate component 208. In this manner, upon draw on the mouthpiece 214, the filter 212 receives the aerosol flowing through the intermediate component 208 of the aerosol source member 200. In some implementations, the filter 212 may comprise discrete segments. For example, some implementations may include a segment providing filtering, a segment providing draw resistance, a hollow segment providing a space for the aerosol to cool, a segment providing increased structural integrity, other filter segments, and any one or any combination of the above. In some implementations, the filter 212 may additionally or alternatively contain strands of tobacco containing material, such as described in U.S. Pat. No. 5,025,814 to Raker et al., which is incorporated herein by reference in its entirety.

In various implementations the size and shape of the intermediate component 208 and/or the filter 212 may vary, for example the length of the intermediate component 208 may be in an inclusive range of approximately 10 mm to approximately 30 mm, the diameter of the intermediate component 208 may be in an inclusive range of approximately 3 mm to approximately 8 mm, the length of the filter 212 may be in an inclusive range of approximately 10 mm to approximately 20 mm, and the diameter of the filter 212 may be in an inclusive range of approximately 3 mm to approximately 8 mm. In the depicted implementation, the intermediate component 208 has a length of approximately 20 mm and a diameter of approximately 4.8 mm (and in some implementations, approximately 7 mm), and the filter 212 has a length of approximately 15 mm and a diameter of approximately 4.8 mm (or in some implementations, approximately 7 mm).

In various implementations, ignition of the heat source 204 results in aerosolization of the aerosol precursor composition associated with the substrate portion 210. Preferably, the elements of the substrate portion 210 do not experience thermal decomposition (e.g., charring, scorching, or burning) to any significant degree, and the aerosolized components are entrained in the air that is drawn through the aerosol source member 200, including the filter 212, and into the mouth of the user. In various implementations, the mouthpiece 214 (e.g., the intermediate component 208 and/or the filter 212) is configured to receive the generated aerosol therethrough in response to a draw applied to the mouthpiece 214 by a user. In some implementations, the mouthpiece 214 may be fixedly engaged to the substrate portion 210. For example, an adhesive, a bond, a weld, and the like may be suitable for fixedly engaging the mouthpiece 214 to the substrate portion 210. In one example, the mouthpiece 214 is ultrasonically welded and sealed to an end of the substrate portion 210.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device, comprising:
an aerosol source member, further comprising:
a substrate portion comprising a nanocellulose material impregnated with an aerosol precursor composition;
a heat source configured to heat the aerosol precursor composition from the substrate portion forming an aerosol; and
an aerosol pathway extending from the substrate portion to a mouth-end of the aerosol delivery device.

2. The aerosol delivery device of claim 1, wherein the heat source comprises either an electrically powered heating element or a combustible ignition source.

3. The aerosol delivery device of claim 1, wherein the heat source is a combustible ignition source comprising a carbon-based material.

4. The aerosol delivery device of claim 1, wherein the heat source is an electrically-powered heating element, and further comprising a power source electronically connected to the heating element.

5. The aerosol delivery device of claim 4, further comprising a controller configured to control the power transmitted by the power source to the heating element.

6. The aerosol delivery device of claim 1, wherein the nanocellulose material comprises cellulose microfibrils, cellulose nanofibrils, cellulose nanocrystals, or combinations thereof.

7. The aerosol delivery device of claim 1, wherein the nanocellulose material comprises tobacco-derived nanocellulose.

8. The aerosol delivery device of claim 1, wherein the nanocellulose material contains at least one average particle size dimension in the range of about 1 nm to about 100 nm.

9. The aerosol delivery device of claim 1, wherein the nanocellulose material is impregnated with one or more polyols at a loading level of about 20% by weight or higher, based on the total weight of the impregnated nanocellulose material.

10. The aerosol delivery device of claim 9, wherein the nanocellulose material is impregnated with the one or more polyols at a loading level of about 50% by weight or higher.

11. The aerosol delivery device of claim 1, wherein the aerosol precursor composition comprises glycerin, propylene glycol, menthol, or combinations thereof.

12. The aerosol delivery device of claim 1, wherein at least a portion of the nanocellulose material is treated to increase hydrophobicity.

13. The aerosol delivery device of claim 12, wherein the treated nanocellulose material is impregnated with a hydrophobic aerosol precursor selected from the group consisting of esters, terpenes, aromatics, and lactones.

14. The aerosol delivery device of claim 13, wherein the treated nanocellulose material is impregnated with one or more of menthol, methyl butyrate, ethyl butyrate, isoamyl acetate, pentyl pentanoate, citral, nerol, limonene, citronella, carvone, eugenol, anisol, benzaldehyde, massoia lactone, sotolon, jasmine lactone, gamma-decalactone, geraniol, and delta-decalactone.

15. The aerosol delivery device of claim 1, wherein the substrate portion is in a particulate or shredded form, in the form of a sheet, or in the form of a film.

16. The aerosol delivery device of claim 15, wherein the sheet or film is substantially free of polymeric binder.

17. The aerosol delivery device of claim 15, wherein the sheet or film is a reconstituted tobacco or botanical sheet or film formed with a polymeric binder.

18. The aerosol delivery device of claim 15, wherein the sheet or film is a nanocellulose sheet or film formed with a polymeric binder, and said sheet or film is substantially free of tobacco and non-tobacco botanicals.

19. The aerosol delivery device of claim 1, wherein the substrate portion further comprises one or more of a burn retardant material and a flavorant.

20. The aerosol delivery device of claim 1, wherein the substrate portion is formed into a substantially cylindrical shape.

21. The aerosol delivery device of claim 1, wherein the substrate portion comprises a series of overlapping layers of a composite substrate sheet, wherein one or more layers comprise the nanocellulose material.

22. The aerosol delivery device of claim 1, wherein the heat source comprises a conductive ink printed on a surface of the substrate portion.

23. The aerosol delivery device of claim 1, wherein the substrate portion is substantially free of tobacco and/or nicotine.

24. The aerosol delivery device of claim 1, wherein the substrate portion further comprises a pharmaceutical agent and/or a non-tobacco botanical.

* * * * *

UNITED STATES PATENT AND TRADEMARK OFFICE
CERTIFICATE OF CORRECTION

PATENT NO. : 11,324,249 B2
APPLICATION NO. : 16/294098
DATED : May 10, 2022
INVENTOR(S) : Andries Don Sebastian et al.

Page 1 of 1

It is certified that error appears in the above-identified patent and that said Letters Patent is hereby corrected as shown below:

On the Title Page

On the page 2, in Column 1, under item (56) "U.S. Patent Documents", Line 55, delete "Dooley" and insert -- Dooly --.

On the page 2, in Column 2, under item (56) "Other Publications", Line 15, delete "Montteal" and insert -- Montreal, --.

On the page 2, in Column 2, under item (56) "Other Publications", Line 19, delete "ofHigh" and insert -- of High --.

In the Claims

In Column 29, Line 19, in Claim 14, delete "anisol," and insert -- anisole, --.

Signed and Sealed this
Fourteenth Day of May, 2024

Katherine Kelly Vidal
*Director of the United States Patent and Trademark Office*